US010085622B2

(12) United States Patent
Walish et al.

(10) Patent No.: US 10,085,622 B2
(45) Date of Patent: Oct. 2, 2018

(54) CONTROL OF A BASKET RETRIEVAL DEVICE

(71) Applicant: GYRUS ACMI, INC., Southborough, MA (US)

(72) Inventors: Judy L. Walish, West Roxbury, MA (US); Kurt Shelton, Bedford, MA (US); Allison B. Dianis, Andover, MA (US)

(73) Assignee: GYRUS ACMI, INC., Southborough, MA (US)

( * ) Notice: Subject to any disclaimer, the term of this patent is extended or adjusted under 35 U.S.C. 154(b) by 82 days.

(21) Appl. No.: 14/850,272

(22) Filed: Sep. 10, 2015

(65) Prior Publication Data

US 2016/0166129 A1 Jun. 16, 2016

Related U.S. Application Data

(60) Provisional application No. 62/091,758, filed on Dec. 15, 2014.

(51) Int. Cl.
*A61B 1/00* (2006.01)
*A61B 1/04* (2006.01)
(Continued)

(52) U.S. Cl.
CPC .......... *A61B 1/0052* (2013.01); *A61B 1/0014* (2013.01); *A61B 1/0051* (2013.01);
(Continued)

(58) Field of Classification Search
CPC .. A61B 1/0014; A61B 1/0125; A61B 17/2909
(Continued)

(56) References Cited

U.S. PATENT DOCUMENTS

| 5,938,588 A * | 8/1999 | Grabover | A61B 1/0057 600/143 |
| 6,676,668 B2 * | 1/2004 | Mercereau | A61B 17/221 606/1 |

(Continued)

FOREIGN PATENT DOCUMENTS

| EP | 2508120 A1 | 10/2012 |
| JP | 2004358012 A * | 12/2004 |
| JP | 2007151595 A | 6/2007 |

OTHER PUBLICATIONS

International Search Report and Written opinion for International Application No. PCT/US2015/049374, dated Dec. 4, 2015.

*Primary Examiner* — Alexandra L Newton
*Assistant Examiner* — Rynae Boler
(74) *Attorney, Agent, or Firm* — The Dobrusin Law Firm, P.C.

(57) ABSTRACT

A medical system is provided comprising a medical device including a handle and a mechanism for moving a distal end of the medical device; an auxiliary medical device comprising a basket retrieval device including a basket sheath disposed over a basket wire and received into a working channel of the medical device; a knob assembly in communication with the basket retrieval device, the knob assembly rotatable so that the basket sheath, wire, or both move within the working channel; and a base removably connecting the auxiliary medical device to the handle wherein the handle and the base are configured to be simultaneously gripped with a hand, and wherein the mechanism is configured to be moved with a first finger to move the distal end of the medical device and the knob assembly is configured to be rotated with a second finger to move the basket sheath wire, or both.

20 Claims, 27 Drawing Sheets

(51) Int. Cl.
*A61B 17/22* (2006.01)
*A61B 1/005* (2006.01)
*A61B 1/018* (2006.01)
*A61B 1/307* (2006.01)

(52) U.S. Cl.
CPC .......... *A61B 1/00085* (2013.01); *A61B 1/018* (2013.01); *A61B 1/307* (2013.01)

(58) Field of Classification Search
USPC .................. 600/104, 113, 131; 606/1, 127
See application file for complete search history.

(56) References Cited

U.S. PATENT DOCUMENTS

| | | | |
|---|---|---|---|
| 7,922,650 B2 | 4/2011 | McWeeney et al. | |
| 2004/0215212 A1* | 10/2004 | Teague | A61B 17/221 606/127 |
| 2005/0065399 A1* | 3/2005 | Sasaki | A61B 1/018 600/106 |
| 2006/0195117 A1* | 8/2006 | Rucker | A61B 1/00137 606/108 |
| 2006/0252993 A1 | 11/2006 | Freed et al. | |
| 2007/0100254 A1 | 5/2007 | Murakami et al. | |
| 2008/0200756 A1 | 8/2008 | Okada et al. | |
| 2009/0024141 A1 | 1/2009 | Stahler et al. | |
| 2009/0105534 A1* | 4/2009 | Nakagawa | A61B 1/00137 600/106 |
| 2009/0157060 A1* | 6/2009 | Teague | A61B 17/221 606/1 |
| 2010/0191224 A1* | 7/2010 | Butcher | A61B 17/221 606/1 |
| 2010/0198015 A1* | 8/2010 | Greenburg | A61B 1/00128 600/131 |
| 2012/0165829 A1 | 6/2012 | Chen et al. | |
| 2014/0171735 A1 | 6/2014 | Galperin et al. | |
| 2014/0171833 A1 | 6/2014 | Matsuno et al. | |
| 2014/0223701 A1 | 8/2014 | Bean et al. | |
| 2014/0243849 A1 | 8/2014 | Saglam et al. | |

* cited by examiner

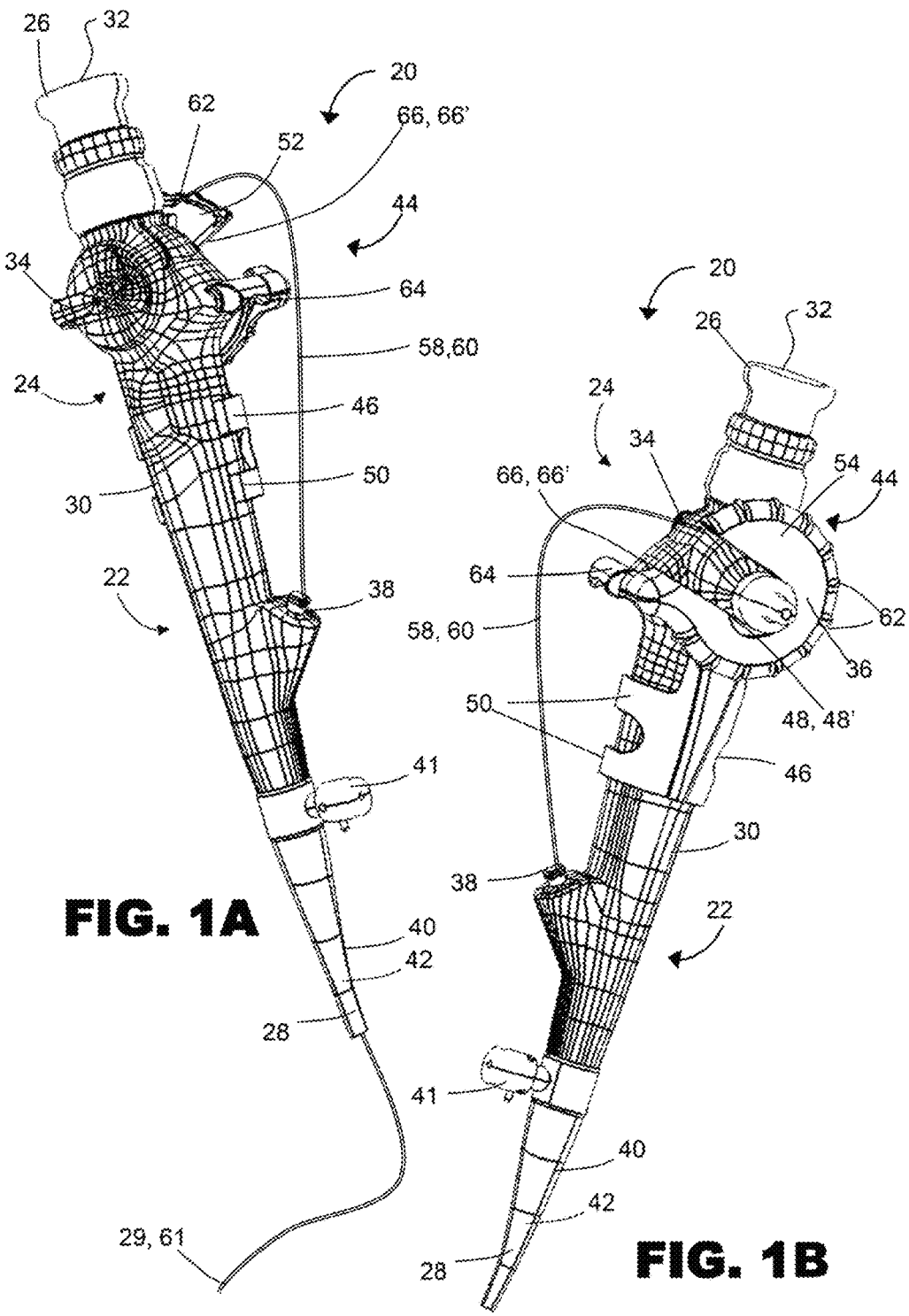

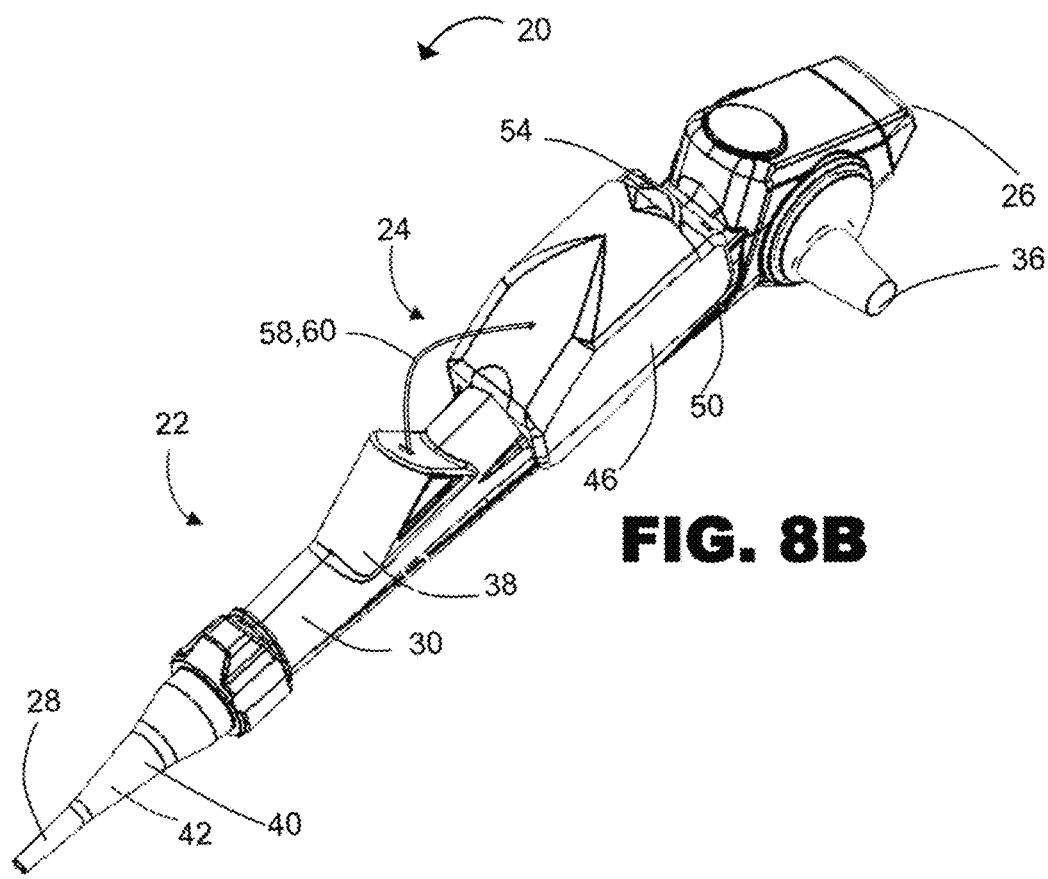

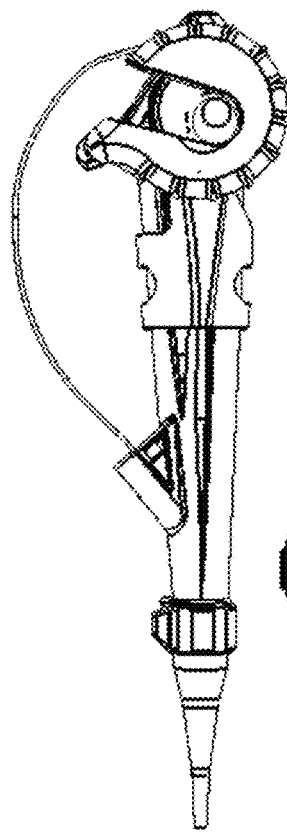 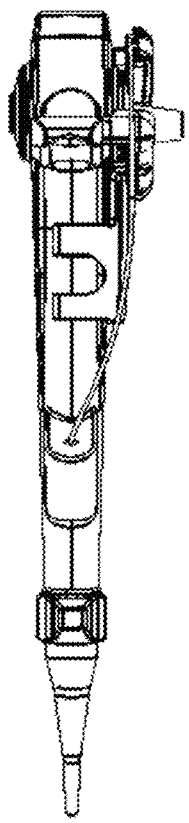 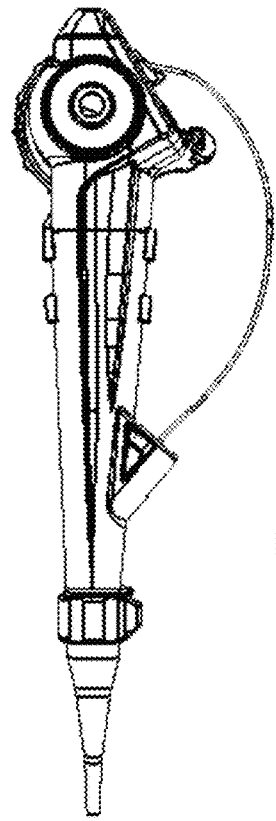 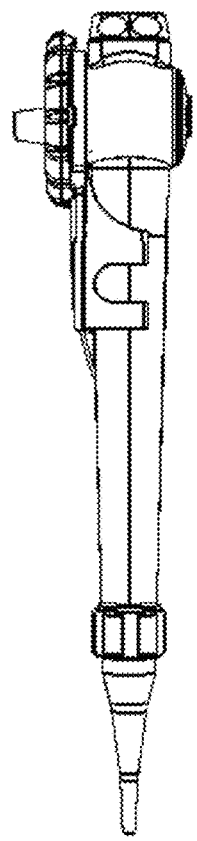
FIG. 12A  FIG. 13A
FIG. 12B  FIG. 13B

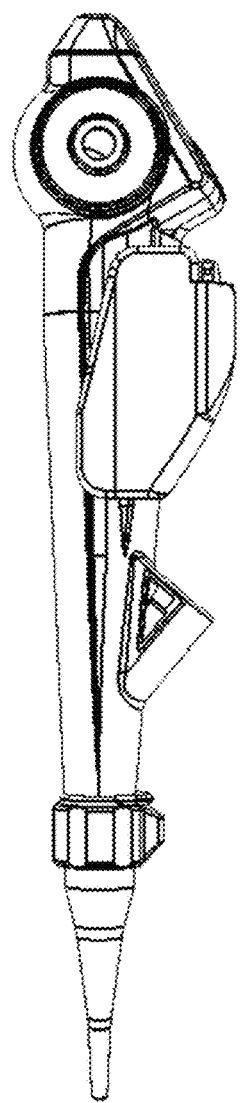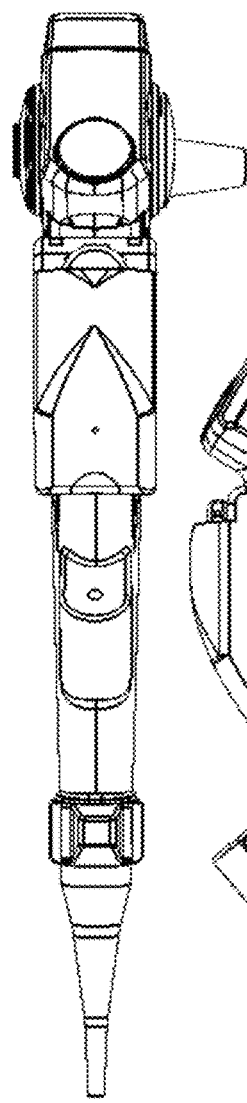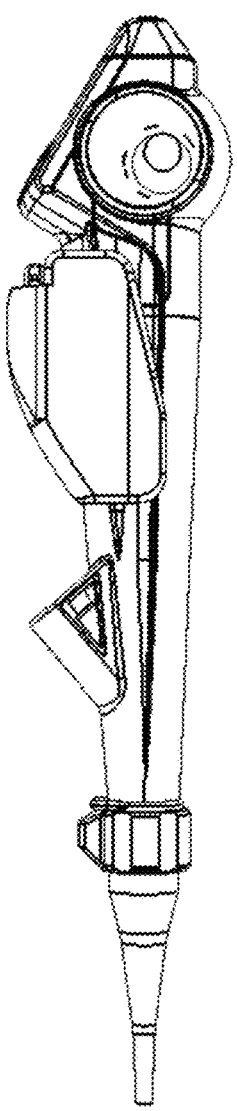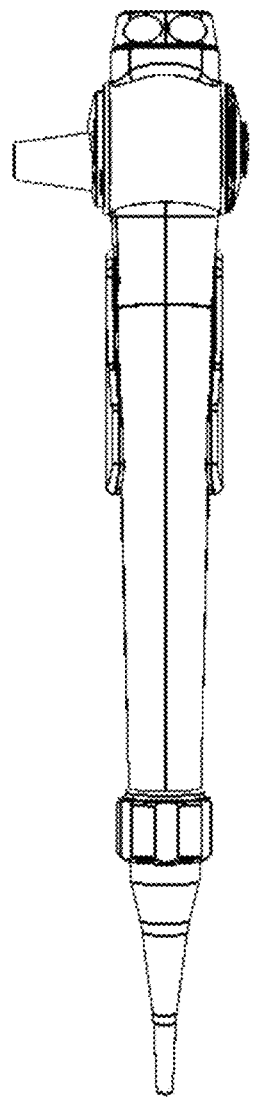
FIG. 27  FIG. 28  FIG. 29  FIG. 30

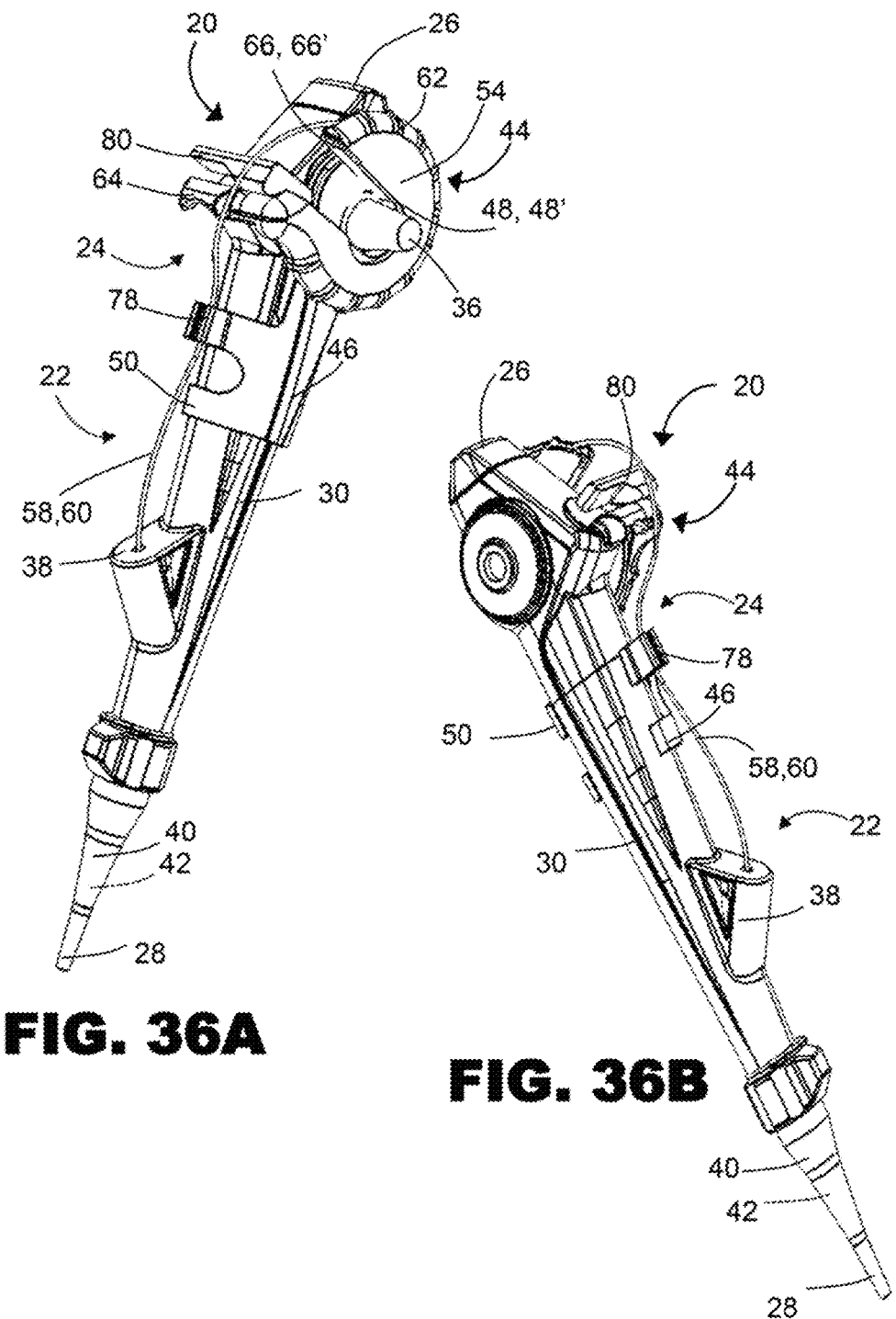

CONTROL OF A BASKET RETRIEVAL DEVICE

FIELD

The present teachings generally relate to a basket retrieval device and more specifically to improved control of a basket retrieval device.

BACKGROUND

Medical devices like endoscopes may be used in medical procedures to gain visual access into an internal location of a patient. Auxiliary medical devices like basket retrieval devices may be used in medical procedures to immobilize and/or retrieve biological matters (e.g., kidney stones, urinary calculi, etc.,) located within an internal location of a patient. In some instances, an endoscope and a basket retrieval device may be connected together and a doctor can control the endoscope with one hand and the basket retrieval device with the other hand. In other instances, the endoscope and the basket retrieval device may be separated, and a doctor can control the endoscope, while an assistant controls the basket retrieval device. It may therefore be appreciated that some medical procedures involving an endoscope and a basket retrieval device may be burdensome and cumbersome. Accordingly, it may be desirable to provide a medical system including a basket retrieval device that can quickly attach to an endoscope so that a doctor can grip and control both devices with a single hand. It may also be desirable to provide a method for quickly attaching a basket retrieval device to an endoscope so that a doctor can grip and control both devices with a single hand.

Some examples of medical systems including basket retrieval devices and endoscopes can be found in U.S. Pat. No. 7,922,650, U.S. Pat. Publication Nos. 2012/0165829, 2014/0243849, 200910024141 and 2008/0200756, and Japanese Publications JP2004358012 and JP2007151595, all of which are incorporated by reference herein in their entirety for all purposes.

SUMMARY

The teachings herein provide a medical system comprising a medical device, the medical device including a handle and a mechanism for moving a distal end of the medical device; an auxiliary medical device, the auxiliary medical device comprising: a basket retrieval device including a basket sheath disposed over a basket wire, the basket sheath, the basket wire, or both are received into a working channel of the medical device; a knob assembly in communication with the basket retrieval device, the knob assembly is rotatable so that the basket sheath, the basket wire, or both move within the working channel of the medical device; and a base connected to the knob assembly, the base removably connecting the auxiliary medical device to the handle of the medical device, wherein the handle and the base are configured to be simultaneously gripped with a hand of a user, and wherein the mechanism is configured to be moved with a first finger of the hand to move the distal end of the medical device and the knob assembly is configured to be rotated with a second finger of the hand to move the basket wire relative to the basket sheath, the distal end of the medical device, or both.

The teachings herein also provide a method comprising providing a medical device including a handle and a tubular portion connected to the handle, the medical device including a moveable mechanism for moving the tubular portion; providing an auxiliary medical device including a base, a knob assembly connected to the base, and a basket retrieval device in communication with the knob assembly, the knob assembly is rotatable for moving the basket retrieval device to accomplish opening or closing of the basket retrieval device as it exits and enters the distal end of the tubular portion; connecting the base of the auxiliary medical device to the handle of the medical device; inserting at least a portion of the basket retrieval device into the tubular portion of the medical device; gripping both the handle and the base with a hand; inserting the tubular portion of the medical device into a patient; moving the mechanism with a first finger of the hand while the hand grips the handle and the base to move the tubular portion inside the patient; and rotating the knob assembly with the first finger or a second finger of the hand while the hand grips the handle and the base to move the basket retrieval device inside the tubular portion, the patient or both.

The teachings herein further provide a medical system including a basket retrieval device that can quickly attach to an endoscope so that a doctor can grip and control both devices with a single hand.

Further yet, the teachings herein provide a method for quickly attaching a basket retrieval device to an endoscope so that a doctor can grip and control both devices with a single hand.

BRIEF DESCRIPTION OF THE DRAWINGS

FIG. 1A illustrates a perspective view of a medical system including a medical device and an auxiliary medical device in accordance with the teachings herein;

FIG. 1B illustrates a perspective view of a medical system including a medical device and an auxiliary medical device in accordance with the teachings herein;

FIG. 8B illustrates a perspective view of a medical system including a medical device and an auxiliary medical device in accordance with the teachings herein;

FIG. 12A illustrates an assembled side view of the medical system of FIGS. 2A and 2B.

FIG. 12B illustrates an assembled front view of the medical system of FIGS. 2A and 2B.

FIG. 13A illustrates an assembled side view of the medical system of FIGS. 2A and 2B.

FIG. 13B illustrates an assembled back view of the medical system of FIGS. 2A and 2B.

FIG. 27 is a side view of the medical system of FIGS. 8A and 8B.

FIG. 28 is a front view of the medical system of FIGS. 8A and 8B.

FIG. 29 is a side view of the medical system of FIGS. 8A and 8B.

FIG. 30 is a back view of the medical system of FIGS. 8A and 8B.

FIG. 36A illustrates a perspective view of a medical system including a medical device and an auxiliary medical device;

FIG. 36B illustrates a perspective view of a medical system including a medical device and an auxiliary medical device in accordance with the teachings herein;

DETAILED DESCRIPTION

Figure 2A:
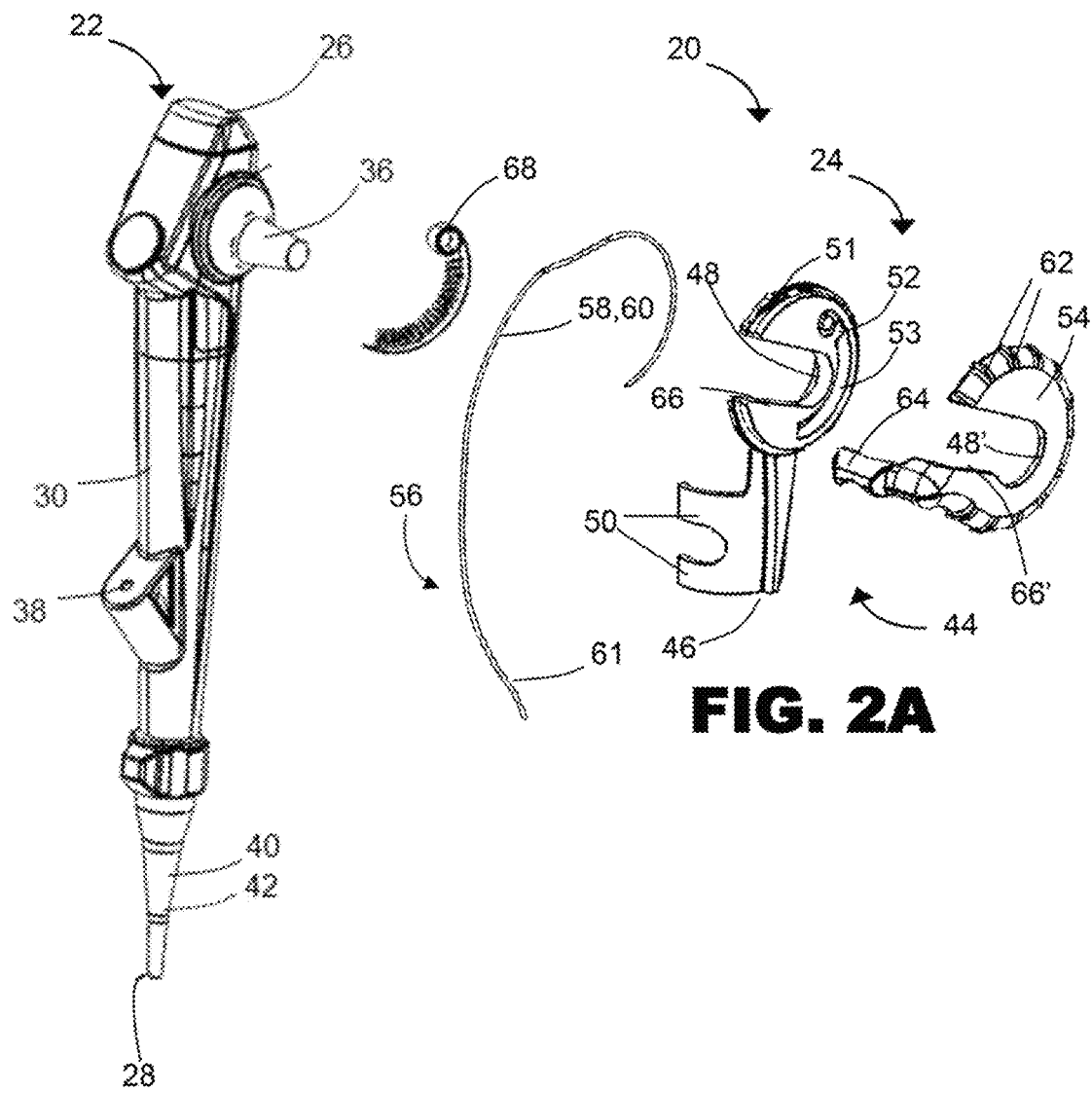
FIG. 2A illustrates an exploded perspective view of a medical system including a medical device and an auxiliary medical device in accordance with the teachings herein.

This application claims priority to and the benefit of U.S. provisional patent application Ser. No. 62/091,758 filed on Dec. 15, 2014, the entire disclosure of which is hereby incorporated by reference as if set forth in its entirety for all purposes. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a medical system including an auxiliary medical device connected to a medical device. The medical system may function to assist in retrieving one or more pieces of matter from a patient during a procedure. The medical system may function to remove particles from a patient during a procedure. The present teachings provide a medical system so that a user such as a doctor, a surgeon, a nurse, or other interested person can hold, grip, and/or maintain the medical system with one hand. The present teachings provide a medical system so that a user can hold, grip, and/or maintain the auxiliary medical device and the medical device simultaneously with one hand. While holding or gripping the medical system with one hand, the present teachings allow a user to operate, control, and/or manipulate the medical device with one or more fingers of the same hand gripping the medical system and also operate, control, and/or manipulate the auxiliary medical device with one or more fingers of the same hand without having to re-grip, reposition, or reconfigure the hand. The present teachings provide a medical system allowing a user to operate, control, manipulate, or a combination thereof the medical device and the auxiliary medical device quickly, efficiently, and comfortably. The present teachings provide a medical system including an auxiliary medical device that can be quickly attached to a medical device, detached from a medical device, or both.

The medical device may include an endoscope, a ureteroscope, or both. The medical device may function to provide a surgeon, a doctor, a nurse, or one or more other interested persons with visual access into a remote location, such as an internal location of a patient. The medical device may function to provide or deliver one or more auxiliary medical devices into an internal location of a patient. The medical device may be used in non-invasive surgery. The medical device may be inserted into an orifice, such as an ear, nose, throat, rectum, or urethra. The medical device may be inserted into a cut in tissue or bone. The medical device may include a handle.

The handle of the medical device may function to provide an area for a user to grip and control the medical system, the medical device, the auxiliary medical device, or a combination thereof. The handle may have a size and shape that can be comfortably gripped and held by a user. The handle may be ergonomic. The handle may include features such as ribs, raised portions, recessed portions, or a combination thereof for controlling and/or directing how and where a user grips and holds the medical device, the medical system, and/or the auxiliary medical device. The handle may be configured for right-handed use, left-handed use, or ambidextrous use. The handle may be fabricated from any suitable material for use in medical procedures. The handle may include one or more ports, plugs, connectors, or a combination thereof for connecting irrigation fluid, suction fluid, surgical tools, illumination, other medical devices, or a combination thereof to the medical system, the medical device, and/or the auxiliary medical device. The handle may include controls for a user to manipulate, operate, move, or control the medical system, the medical device, and/or the auxiliary medical device with one or more fingers of the same hand gripping or holding the handle. For example, the handle may provide power controls, sensing controls, irrigation controls, suction controls, illuminating controls, basket retrieval controls, or a combination thereof for a user to actuate with one or more fingers while maintaining a grip on the handle. The handle may be located at a proximal end or a proximal portion of the medical device. The handle may be configured for receiving thereon an auxiliary medical device. The handle may be configured so that an auxiliary medical device, a clip, a base, one or more resilient fingers, or a combination thereof can quickly and easily attach thereto. The handle may include one or more notches, slots, recesses or a combination thereof for attaching thereto the auxiliary medical device, the base, the one or more resilient fingers, or a combination thereof in a specific orientation and/or at a specific location. The handle may include one or more features for axially, radially, and/or longitudinally positioning, locating, and/or maintaining the auxiliary medical device on the handle, relative to the handle, relative to a proximal end of the medical device, relative to a working channel, relative to a tubular portion, or a combination thereof. A viewing device may be located at a proximal end of the handle.

The viewing device may function to provide a viewing area or window for observing a feature of interest located at or near a distal viewing end of the medical system, the medical device, or both. The viewing device may be a viewing lens. The viewing device may include an eyepiece. The viewing device may include a gripping area for holding, adjusting, or focusing the viewing device. The viewing device may include a generally circular cross-section. The viewing device may function to provide an output so that an image can be displayed on a monitor. The viewing device may be integrally formed with the medical device, the handle, or both. The viewing device may be removably connected to the handle. The viewing device may include a threaded portion for threadably engaging and disengaging a mating threaded portion on the handle. The viewing device may be adjustable. A mechanism may be located near the viewing device.

The mechanism may function to control a distal end, a distal portion, a tubular portion, or a combination thereof of the medical system, the medical device, or both. The mechanism may function to move, manipulate, articulate, reposition, bend, deflect, rotate, direct, extend, retract, or a combination thereof a distal end, a distal portion, a tubular portion, or a combination thereof of the medical system and/or the medical device. The mechanism may include one or more levers, buttons, knobs, actuators, joysticks, or a combination thereof. The mechanism may be mechanical, electrical, electromechanical, or a combination thereof. The mechanism may be a ratchet. The mechanism may be moved, rotated, or actuated in a first direction, a second direction, or both. One or more wires, electrical wires, mechanisms, components, gears, or a combination thereof may connect the mechanism to a distal end, a distal portion, a tubular portion, or a combination thereof of the medical system and/or the medical device. The mechanism may be moved, engaged, actuated, manipulated, or a combination thereof with one or more fingers of the same hand gripping the handle without repositioning, re-gripping, or reconfiguring the hand. The mechanism may include one or more markings, indicators, engravings, or a combination thereof to assist a user in determining how much or how far to move, manipulate, articulate, reposition, bend, deflect, rotate, direct, extend, retract, or a combination thereof a distal end, a distal portion, a tubular portion, or a combination thereof of the medical system and/or the medical device. A connector port may be located near the mechanism.

The connector port may function to connect or provide illumination to the medical system, the medical device, the auxiliary medical device, or a combination thereof. The connector port may be or may include a plug, a connector, a cap, a notch, an undercut, a flange, a quick-connect, a threaded portion, or a combination thereof. The connector port may be connected to a light source. The connector port may be located on the handle generally opposite the mechanism. The connector port may be located near a proximal end of the handle. The connector port may be integrally formed with the handle or connected thereto. The connector port may function to engage or be engaged by at least a portion of the auxiliary medical device. The connector port may at least partially retain and align the auxiliary medical device with the medical device, the medical system or both. The connector port may function to axially align, radially align, and/or longitudinally align the auxiliary medical device with the medical system, the medical device, a working channel, a working channel port, or a combination thereof.

The working channel port may function to provide access to a working channel located within the tubular portion of the medical device. The working channel port may include a connector, a port, a flange, a one-way fitting, a quick-connect, or a combination thereof for receiving and/or engaging at least a portion of an auxiliary medical device, a basket retrieval device, or both. The working channel port may be at least partially sealed so that foreign objects, contaminants, or both are restricted or prevented from entering the working channel port, the working channel, or both. The working channel port may be integrally formed with the handle, the medical device, or both, or may be connected thereto. The working channel port may be located towards a distal end, in a distal end region (e.g., the last 15 percent or less or last 10 percent or less by distance) of the handle. The working channel port may be radially located between the mechanism and the connector port. The working channel port may be generally aligned with the auxiliary medical device, the basket retrieval device, the tubular portion, or a combination thereof.

The tubular portion may function to be inserted into an internal location of a patient. The tubular portion may be the leading portion of the medical device, the medical system, or both (i.e., the first portion entering a patient). The tubular portion may be a distal portion of the medical device. The tubular portion may be integrally formed with the handle. The tubular portion may be connected to the handle. The tubular portion may include a generally circular cross-section. The tubular portion may have a toroidally shaped cross section. The tubular portion may include a through hole, a hollow portion, a recess, an aperture, or a combination thereof. The tubular portion may be elongated and may taper from a proximal end towards a distal end. The tubular portion may be fabricated from a material suitable for medical procedures. The tubular portion may be fabricated from a material suitable for insertion into an internal location of a patient. The tubular portion may be flexible, rigid, or both. The tubular portion may be moved or controlled using one or more controls located on the handle. For example, while gripping the handle with one hand, a user may move, engage, articulate, manipulate, or a combination thereof the mechanism with one or more fingers of the same hand, to move, manipulate, articulate, reposition, bend, deflect, rotate, direct, extend, and/or retract the tubular portion. The tubular portion may include an internal seal check port, a pressure relief valve, or both.

The internal seal check port, the pressure relief valve, or both may provide access to the tubular portion, the working channel, or both so that fluid, pressure, or both can be released therefrom. The internal seal check port, the pressure relief valve, or both may be used to check the seal of an internal mechanism. The internal seal check port, the pressure relief valve, or both may be configured so that a pump and a dial can be connected to the tubular portion. The pump may be configured to pressurize the internal sealed mechanism. The pump may be configured to determine if pressure can be sustained therein. If the pump determines there is too much pressure, the pressure release valve may reduce or relieve the pressure therein. The tubular portion may include one or more working channels.

The one or more working channels may function to provide one or more passageways, conduits, lumen, or a combination thereof for one or more basket retrieval devices, basket wires, basket sheaths, irrigation tubes, suction tubes, surgical tools, lasers, or a combination thereof to extend through the tubular portion. The working channel may provide a passageway for one or more control wires, electrical wires, mechanisms, components, gears, basket retrieval devices, basket wires, basket sheaths, or a combination thereof to extend from the mechanism, the auxiliary medical device, the handle to the tubular portion, a distal end of the medical system, and/or the medical device. The working channel may function to at least temporarily store retrieved matters (e.g., kidney stones, urinary calculi, etc.) removed from an internal location of the patient with the basket retrieval device. The working channel may extend through at least a portion of the tubular portion, the handle, or both.

The auxiliary medical device may be a basket retrieval device that may function to retrieve a substance of interest such as biological matter (e.g., kidney stones, urinary calculi, etc.) located within an internal location of the patient. The auxiliary medical device may function to immobilize one or more kidney stones relative to a laser beam, which may be used to fragment the one or more stones into smaller pieces for retrieval and removal with the auxiliary medical device. The auxiliary medical device may be connected to the medical device to form the medical system. The auxiliary medical device may be removably and securely connected to the handle of the medical device. The auxiliary medical device may be connected to the handle of the medical device in one or more configurations. The one or more configurations may be predetermined. Once connected, a user may grip at least a portion of the medical device and at least a portion of the auxiliary medical device simultaneously with one hand. Once connected, a user may grip the medical system with one hand and operate the medical device with one or more fingers of the same hand and also operate auxiliary medical device with one or more fingers of the same hand without re-gripping or repositioning the hand gripping the medical system. The medical system may be gripped and/or held with a right hand, a left-hand, or both. The auxiliary medical device may be inserted into an orifice, such as a nose, throat, rectum, or urethra. The auxiliary medical device may include a base.

The base may function to connect or attach the auxiliary medical device to the medical device, the handle, or both. The base may function to removably connect or attach the auxiliary medical device to the medical device, the handle or both. The base may be configured to engage the handle so that the auxiliary medical device is sufficiently retained thereon. The base may be configured so that the auxiliary medical device can be connected or attached to the medical device in one or more configurations and/or orientations. The base may include one or more ribs, recesses, notches, grooves, or a combination thereof that may engage mating ribs, recesses, notches, grooves, or a combination thereof. The base may surround at least a portion of the handle when connected to the medical device. A permanent or temporary adhesive, tape, hook and loop fastener, one or more other mechanical fasteners or couplers, or a combination thereof may connect the base, the one or more fingers, the auxiliary medical device, or a combination thereof to the medical device. The base may be fabricated from a material that is at least partially rigid, at least partially flexible, or both so that the base can removably engage the handle. The base may be resilient. The base may be fabricated from a material suitable for use in medical procedures. The base may be fabricated from a material that can be gripped by a user. The base may include one or more ridges, notches, and/or grooves for a user to comfortably grip the base. The base may be ergonomically designed and configured so that a user can comfortably and simultaneously grip the base and the handle with one hand. The base may connect to the handle so that a user can grip the base and the handle simultaneously while also manipulating, operating, and/or controlling the medical device, the mechanism, the auxiliary medical device, the basket retrieval device, or a combination thereof with the same hand. The base may include one or more fingers.

The one or more fingers may function to connect the base to the handle, the medical device, or both. The one or more fingers may function to securely connect or snap the auxiliary medical device to or onto the medical device. The one or more fingers may include two or more fingers, three or more fingers, preferably four or more fingers, or even five or more fingers. The one or more fingers may at least partially wrap around the handle. The one or more fingers may engage one or more notches, slots, recesses, or a combination thereof so that the auxiliary medical device can engage the handle in one or more predetermined configurations and/or orientations. The one or more fingers may engage the handle so that the auxiliary medical device does not move relative to the medical device. The one or more fingers may be flexible so that a user can flex the fingers outwardly to attach the base to the handle. The one or more fingers may be at least partially resilient so that when the fingers are flexed outwardly to connect to the handle, the fingers can return to their original pre-flexed configuration to engage the handle. The one or more fingers may be integrally formed with the base. The one or more fingers may be connected to the base. A permanent or temporary adhesive, tape, hook and loop fastener, or one or more other mechanical couplers may be used to connect the one or more fingers, the base, the auxiliary medical device, or a combination thereof to the handle, the medical device, or both. A knob assembly including an inner knob and an outer knob may be connected to the base.

The inner knob may function to engage the medical device and at least a portion of the basket retrieval device, the basket sheath, and/or the basket wire so that when the inner knob is moved or rotated, the basket retrieval device moves out of and into the distal end of the tubular portion such that the basket retrieval device opens and closes. The inner knob may be connected to a proximal end or a proximal portion of the base. The inner knob may be generally circular. The inner knob may include an opening for engaging the handle, the connector port, or both. The opening may engage the connector port so that the basket retrieval device is generally aligned with the medical device, the tubular portion, the working channel port, the working channel, or a combination thereof in one or more orientations and/or configurations. The inner knob may include a slot in communication with the opening so that the inner knob does not interfere with one or more wires, tubes, and/or other features of the medical system. The inner knob may include a groove at least partially extending around a circumference thereof. The groove may be configured to engage at least a portion of the basket retrieval device, the basket sheath and/or the basket wire. The opening may engage the connector port so that the inner knob can at least partially rotate in a first direction, a second direction, or both. The opening may engage the connector port so that the inner knob can at least partially rotate generally about the connector port in a first direction, a second direction, or both. The inner knob may be in rotational communication with an outer knob. The inner knob may at least partially rotate about the connector port between a non-rotated position and a rotated position. The inner knob may be in communication with the outer knob so that when the outer knob rotates the inner knob correspondingly rotates, and vice versa.

The outer knob may function to provide a user with the ability to move, actuate, manipulate, and/or control the auxiliary medical device, the basket retrieval device, the basket sheath, the basket wire, the basket, or a combination thereof. The outer knob may be generally circular. The outer knob may be connected to the inner knob. The outer knob may be integrally formed with the inner knob. The outer knob and the inner knob may be the same component. The outer knob may include gears engaging mating gears on the inner knob so that when the outer knob is rotated the inner knob also rotates, and vice versa. The gears or projections extending between the knobs may be step up or step down gears to change the rotation ratio there between. The outer knob may include an opening for engaging the connector port of the medical device. The opening of the outer knob may engage the connector port so that the outer knob can generally rotate about the connector port between a non-rotated position and a rotated position. The opening of the outer knob may engage connector port so that the outer knob can rotate in a first direction, a second direction, or both. The opening of the outer knob may engage the connector port so that the outer knob can at least partially rotate generally about the connector port in a first direction, a second direction, or both. The opening of the outer knob may engage the connector port so that the basket retrieval device is generally aligned with the medical device, the tubular portion, the working channel port, the working channel, or a combination thereof. The outer knob may include a slot connected to the opening so that the outer knob does not interfere with one or more wires, tubes, and other features of the medical system. The opening and/or the slot of the outer knob may be generally aligned with the opening and/or the slot of the inner knob. The outer knob may include one or more gripping ridges disposed about an outer circumference of the outer knob. The outer knob may include one or more levers. The one or more levers may be integrally formed with the outer knob or may be connected thereto. The one or more levers may pivot about the outer knob, or may be fixedly connected thereto. The one or more gripping ridges, levers, or both may be engaged with one or more fingers of the same hand gripping the medical device, the handle, the base, the medical system, the auxiliary medical device, or a combination thereof so that the outer knob can be rotated in a first direction, a second direction, or both from a non-rotated position to a rotated position and vice versa.

The auxiliary lever may function to provide a user with the ability to move the inner knob, the outer knob, or both, individually or together. Movement, manipulation, or rotation of the auxiliary lever may cause the inner knob to move independently of the outer knob; cause the outer knob to move independently of the inner knob; or cause both the inner knob and the outer knob to move together. The auxiliary lever may be manipulated, moved, or rotated to move, deflect, bend, control, or a combination thereof a tubular portion of the medical device. The auxiliary lever may be manipulated or moved to move at least a portion of the basket retrieval device, the basket sheath, and/or the basket wire. The auxiliary lever may be manipulated or moved causing both the basket wire and the basket to collapse and/or retract into the basket sheath, the distal end of the medical device, or both and the distal end of the medical device to move. The auxiliary lever may include a generally circular portion for engaging the inner knob, the outer knob, the medical device, or a combination thereof. The auxiliary lever may be connected to, fixed to, or placed between the inner knob, the outer knob, or both. The auxiliary lever may include one or more arms. The one or more arms may extend at an angle from a circular body portion of the auxiliary lever. The one or more arms may mirror a shape of an arm of the outer knob. The one or more arms may have a complementary fit to the arm of the lever of the outer knob. The one or more arms may be movable with a first finger, a second finger, or both of the same hand gripping the handle of the medical device. The one or more arms may be movable independent of the arm of the outer knob; moveable with the arm of the outer knob; or both.

Rotating the outer knob from the non-rotated position to the rotated position may function to move or open and close the basket sheath, the basket wire, and/or the basket relative to the tubular portion of the medical device. Rotating the outer knob to the rotated position may function to move, expand, extend, or a combination thereof the basket sheath, the basket wire, and/or the basket from the tubular portion of the medical device. Rotating the outer knob to the rotated position may function to extend, expand, or both the basket wire and/or the basket out of a distal end of the basket sheath.

Rotating the outer knob from the rotated position to the non-rotated position may function to move the basket sheath, the basket wire, and/or the basket relative to the tubular portion of the medical device. Rotating the outer knob to the non-rotated position may function to move the basket sheath, the basket wire, and/or the basket back into the tubular portion of the medical device. Rotating the outer knob to the non-rotated position may function to collapse or retract the basket wire and/or the basket back into a distal end of the basket sheath. The outer knob may be rotated in a direction that is generally perpendicular to the direction that the basket retrieval device moves relative to the tubular member. The outer knob may be rotated in a direction that is generally the same as the direction that the basket retrieval device moves relative to the tubular member. A biasing member, such as a spring in communication with the medical device, the knob assembly, the basket retrieval device, or a combination thereof may function to move or rotate the knob assembly to the non-rotated position. The biasing member may be a torsion spring, a constant force spring, a circular spring, or a combination thereof. The outer knob, the inner knob, or both may include a groove for receiving and/or engaging the biasing member.

The basket retrieval device may include a basket sheath, a basket wire disposed within the sheath and a basket at a distal end of the basket wire. One or more of the basket retrieval device, the basket sheath, and the basket wire may be in communication with the knob assembly, the inner knob, the outer knob, or a combination thereof. The basket sheath, the basket wire, or both may be at least partially disposed around the inner knob, the outer knob, or both. The basket wire, and/or the basket, may function to move, expand, retract, orient, or a combination thereof relative to the basket sheath, the tubular portion, or both when the inner knob, the outer knob, or both are rotated. At least a portion of the basket sheath, the basket wire, or both may extend from around the inner knob, the outer knob, or both into the working channel port and into the working channel. A track or a guide may be positioned near the inner knob, the outer knob, or both for guiding or directing the basket sheath and/or the basket wire towards the working channel port. The track or the guide may be movable relative to the inner knob, the outer knob, or both. At least a portion of the basket sheath, the basket wire, or the basket may be positioned near a distal end of the tubular portion, the medical device, the medical system, or combination thereof. The basket sheath, the basket wire, and/or the basket may function to protrude, extend, or both from a distal end of the tubular portion when the inner knob, the outer knob, or both are rotated to the rotated position. The basket wire, the basket or both may function to protrude and/or extend from the basket sheath when the inner knob, the outer knob, or both are rotated from the non-rotated position to the rotated position. The basket may protrude, extend, and/or expand from a distal end of the basket sheath when the inner knob, the outer knob, or both are rotated from the non-rotated position to the rotated position. When the basket protrudes, extends and/or expands from the basket sheath, the tubular portion, or both, the basket may function to retrieve and/or capture biological matters (e.g., kidney stones, urinary calculi, etc.) located within an internal the location of the patient. When the basket protrudes, extends and/or expands from the basket sheath, the basket may function to immobilize kidney stones relative to a laser fiber, which may be used to fragment stones into smaller pieces for retrieval and removal with the basket. The basket wire may function to retract and/or collapse back into the basket sheath, the tubular portion, or both when the inner knob, the outer knob, or both are rotated to the non-rotated position. When the basket retracts into the sheath, the tubular portion, or both, the basket may retain the biological matter (e.g., kidney stones, urinary calculi, etc.) so that the biological matter can be removed from within the internal the location of the patient.

FIGS. 1A, 1B, 2A, and 2B illustrate a medical system 20 including a medical device 22 and an auxiliary medical device 24. The medical device 22 includes a proximal end 26 and a distal portion 28. The proximal end 26 of the medical device 22 includes a handle 30 and a viewing device 32. The handle 30 includes a mechanism 34 for moving, deflecting, bending, controlling, or a combination thereof a tubular portion 40 extending from the handle 30. The handle 30 includes a connector port 36 for connecting illumination, video imaging, or both to the medical system 20, the medical device 22, or both. The handle 30 includes a working channel port 38 providing access to a working channel 42 located within at least a section of the tubular portion 40, the handle 30, or both. The viewing device 32 provides a user with the ability to view an area of interest located at or near a distal end 29 of the medical device 22. The tubular portion 40 includes a port or pressure relief valve 41.

The auxiliary medical device 24 is connected to the medical device 22. The auxiliary medical device 24 includes a knob assembly 44 connected to a base 46. The base 46 includes one or more resiliently flexible fingers 50 for engaging the handle 30 to connect the auxiliary medical device 24 to the medical device 22. The knob assembly 44 includes an inner knob 52 and an outer knob 54 connected to the inner knob 52. The inner knob 52 includes a groove 51 for engaging at least a portion of the basket retrieval device 56. The basket retrieval device 56 includes a basket sheath 60, a basket wire 58, and a basket 61 at a distal end of the basket wire 58. Openings 48, 48' in each of the inner and outer knobs 52, 54, respectively, engage the connector port 36 to connect the auxiliary medical device 24 to the medical device 22. The auxiliary medical device 24 is generally aligned with the medical device 22 so that at least a portion of the basket sheath 60, basket wire, 58, basket 61, or a combination thereof can be received into the working channel port 38 and into the working channel 42 of the medical device 22. The inner knob 52 includes a groove 53 for engaging a biasing member 68. The outer knob 54 includes at least one gripping ridge 62 and lever 64 so that a user can engage and rotate the knob assembly 44 with a first finger to the rotated position 72 (See FIG. 3A) to move and/or deploy the basket retrieval device 56 while gripping the handle 30, the base 46, or both with the same hand. While the user grips the handle 30, the base 46, or both, the user can use the same finger or a second finger of the same hand to move the mechanism 34 to move, deflect, bend and/or control the tubular portion 40 of the medical device 22. A biasing member 68 in communication with the knob assembly 44 assists the user in moving the knob assembly 44 from the rotated position 72 to the non-rotated position 70 (See FIG. 3B) to retract the basket retrieval device 56 into the basket sheath 60. The inner and outer knobs 52, 54 each include a slot 66, 66', respectively, providing clearance for tubes, lines, etc. (not illustrated) extending from the medical system 20, the medical device 22, the auxiliary medical device 24, or a combination thereof.

Figure 3A:
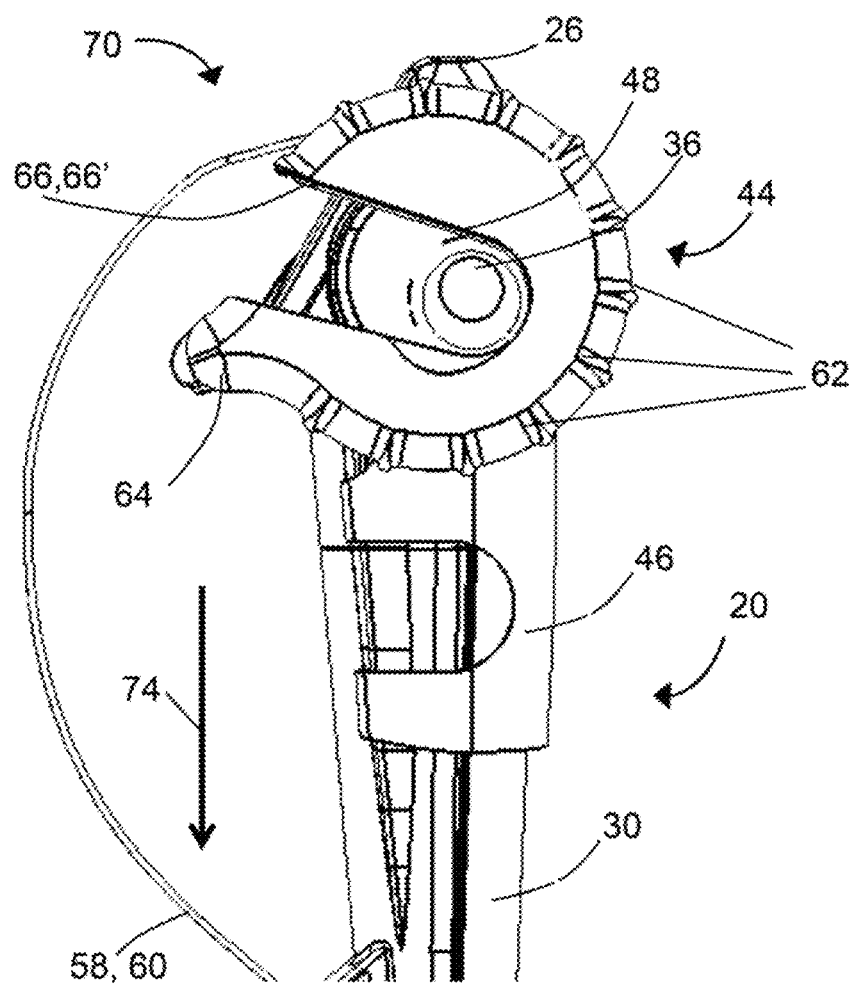
FIG. 3A illustrates a partial perspective view of a medical system: including a medical device and an auxiliary medical device in accordance with the teachings herein, the auxiliary medical device is illustrated in a non-rotated position.
Figure 3B:
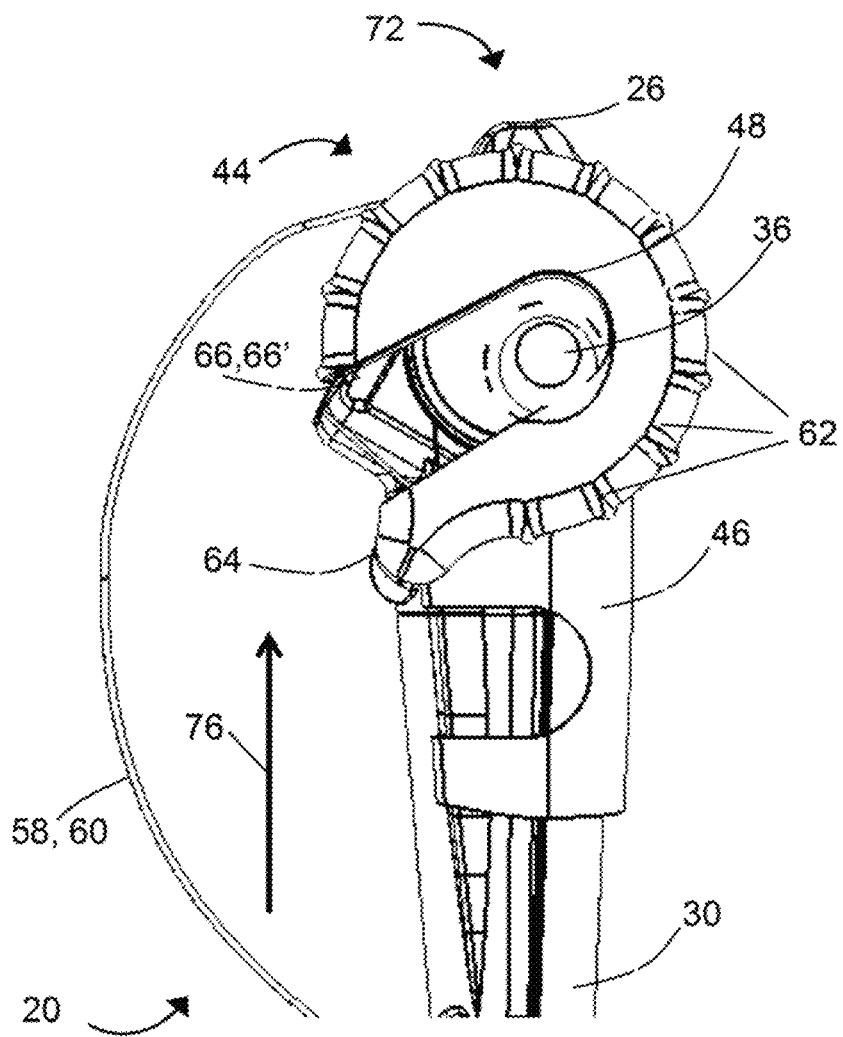
FIG. 3B illustrates a partial perspective view of a medical system including a medical device and an auxiliary medical device in accordance with the teachings herein, the auxiliary medical device is illustrated in a rotated position.

FIGS. 3A and 3B illustrate partial views of the medical system 20. FIG. 3A illustrates the knob assembly 44 in a non-rotated position 70, and FIG. 3B illustrates the knob assembly 44 in a rotated position 72. During use, a user can grip the handle 30, the base 46, or both with one hand and use a first finger of the same hand to engage one or more of the ridges 62, the lever 64, or both to rotate the knob assembly 44 from the non-rotated position 70 in FIG. 3A to the rotated position 72 of FIG. 3B and vice versa. Rotating the knob assembly 44 generally in the direction of the arrow 74 causes the basket wire 58 and/or the basket sheath 60 to move or deploy the basket 61 (not illustrated here) from the basket sheath 60, the working channel 42, the distal portion 28 of the medical device 22, the tubular portion 40, or a combination thereof. Rotating the knob assembly 44 generally in the direction of the arrow 76 in FIG. 3B causes the basket wire 58, and/or the basket 61 to retract or move back into the basket sheath 60, the working channel 42, the distal portion 28 of the medical device 22, the tubular portion 40, or a combination thereof. Accordingly, the direction that the knob assembly 44 is rotated in (i.e., the direction of the arrows 74, 76) generally corresponds to the direction that the basket sheath 60, the basket wire 58, and/or the basket 61 moves relative to the working channel 42, the tubular portion 40, and/or the distal portion 28 of the medical device 22. The biasing member 68 (not illustrated here) helps move the knob assembly 44 from the rotated position 72 to the non-rotated position 70. While the user grips the handle 30, the base 46, or both, the user can use a second finger of the same hand to move the mechanism 34 (not illustrated here) to move, deflect, bend and/or control the tubular portion 40 of the medical device 22.

Figure 4A:
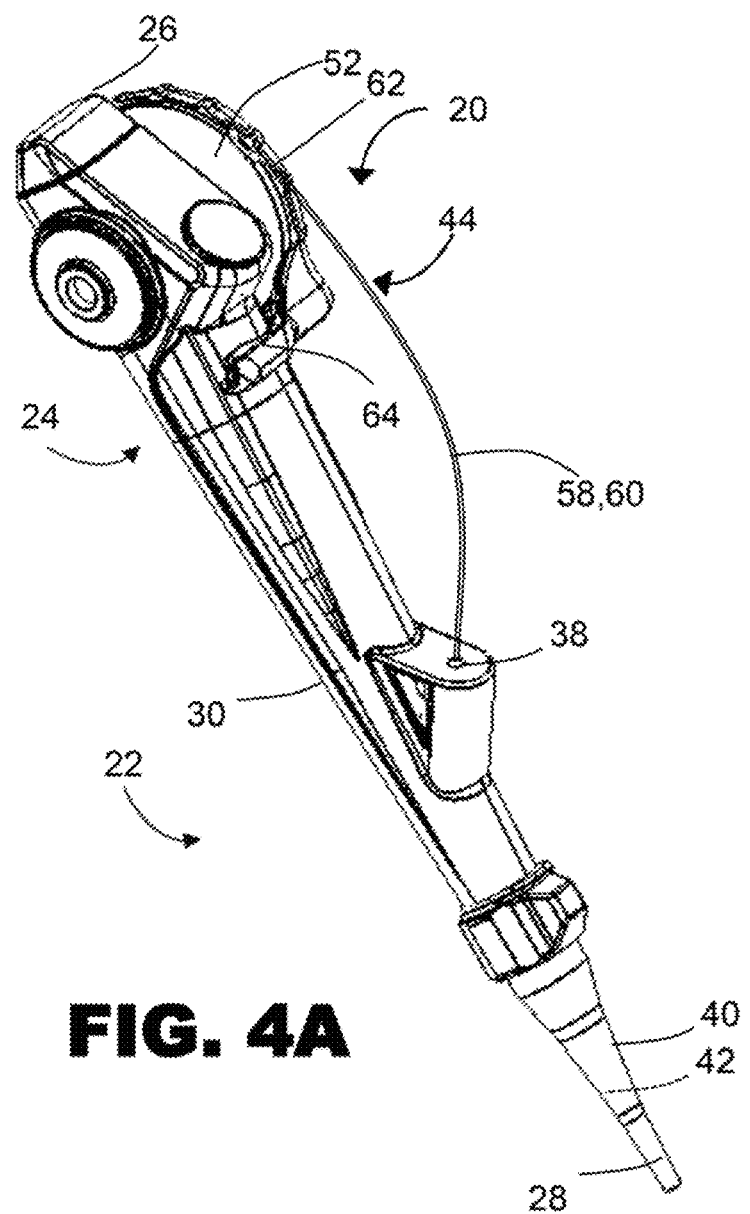
FIG. 4A illustrates a perspective view of a medical system including a medical device and an auxiliary medical device.
Figure 4B:
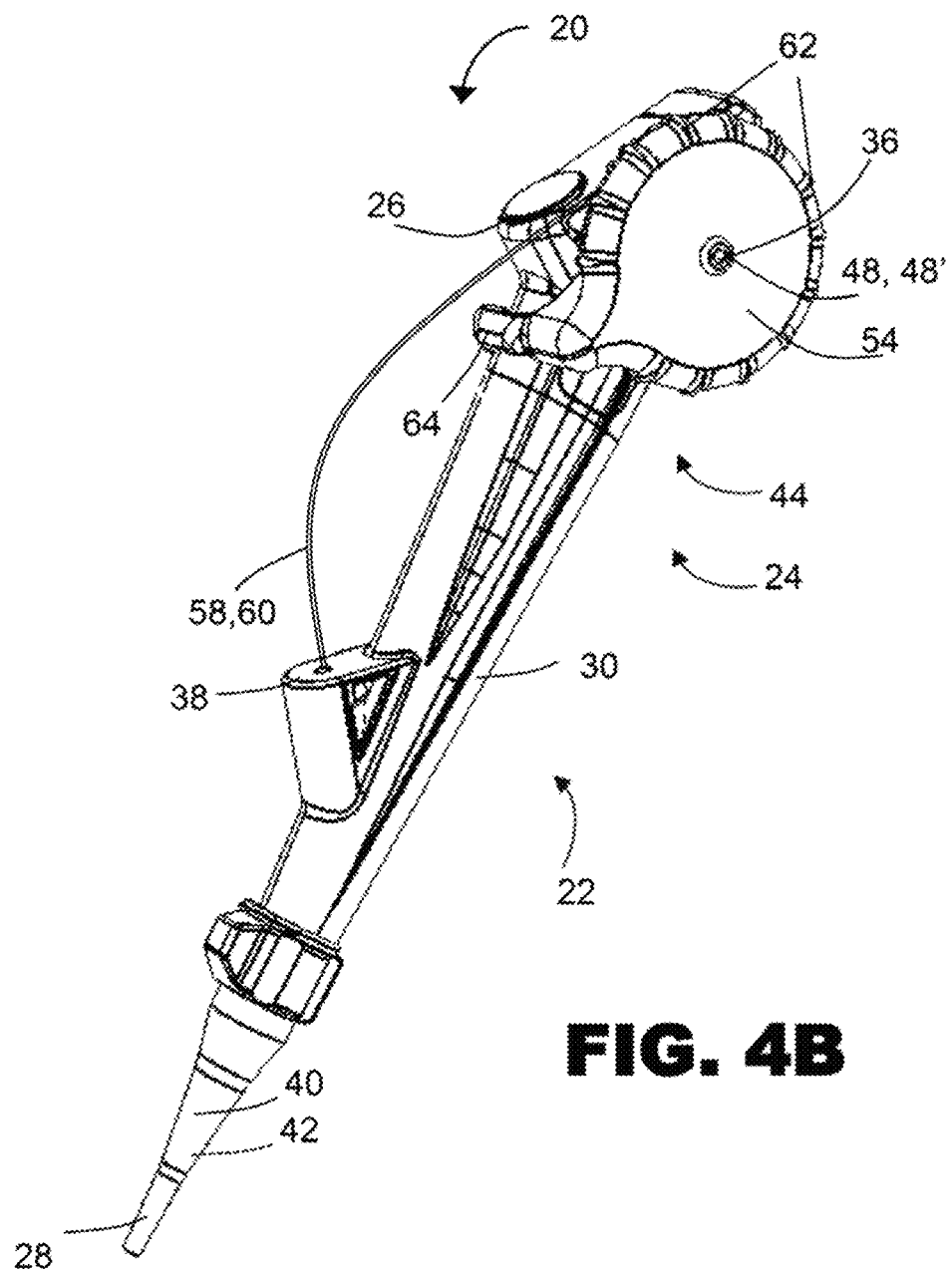
FIG. 4B illustrates a perspective view of a medical system including a medical device and an auxiliary medical device.
Figure 5:
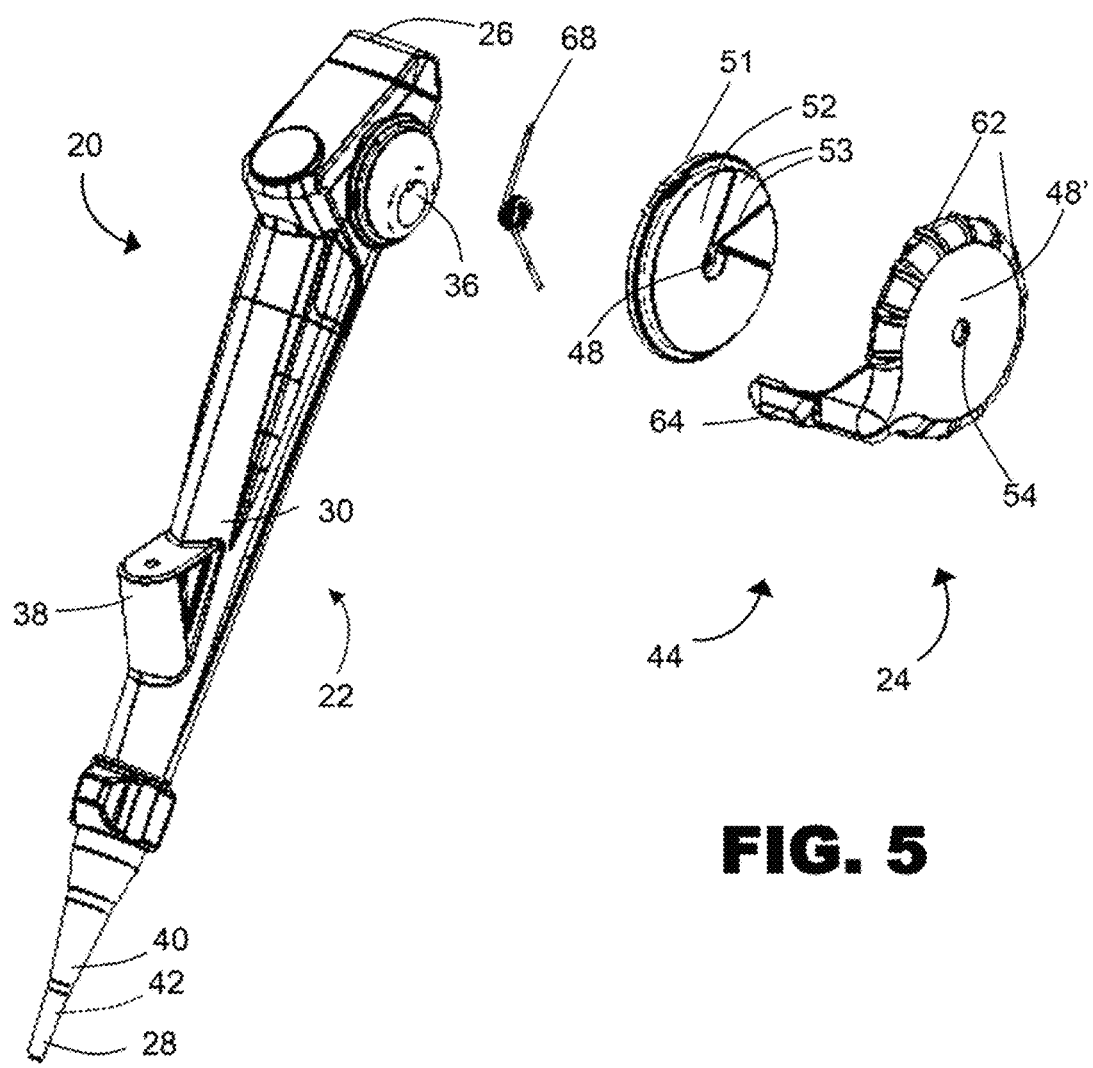
FIG. 5 illustrates an exploded perspective view of a medical system including a medical device and an auxiliary medical device.

FIGS. 4A, 4B, and 5 illustrate a medical system 20 including a medical device 22 and an auxiliary medical device 24. The medical device 22 extends between a proximal end 26 and the distal end 29 (not illustrated here). The proximal end 26 of the medical device 22 includes a handle 30. The handle 30 includes a moveable mechanism 34 (not illustrated here) for moving, deflecting, bending, controlling, or a combination thereof a tubular portion 40 of the medical device 22 connected to the handle 30. The handle 30 includes a connector port 36 for attaching illumination, video imaging, or both to the medical system 20, the medical device 22, or both. The handle 30 includes a working channel port 38 providing access to a working channel 42 located within at least a section of the tubular portion 40, the handle 30, or both.

The auxiliary medical device 24 is connected to the medical device 22. The auxiliary medical device 24 includes a knob assembly 44. The knob assembly 44 includes an inner knob 52 and an outer knob 54 connected to the inner knob 52. The inner knob 52 includes a groove 51 for engaging at least a portion of the basket sheath 60 and basket wire 58. A basket 61 is located at a distal end of the basket wire 58 (also not illustrated here). Openings 48, 48' in each of the inner and outer knobs 52, 54, respectively, engage the connector port 36 to connect the auxiliary medical device 24 to the medical device 22. Openings 48, 48' in each of the inner and outer knobs 52, 54, respectively, engage the connector port 36 to connect the auxiliary medical device 24 to the medical device 22. The auxiliary medical device 24 is generally aligned with the medical device 22 so that at least a portion of the basket sheath 60, basket wire 58 and/or the basket 61 can be received into the working channel port 38 and into the working channel 42 of the medical device 22. The inner knob 52 includes a groove 53 for engaging a biasing member 68. The outer knob 54 includes at least one gripping ridge 62 and lever 64 so that a user can engage and rotate the knob assembly 44 with a first finger to move the basket sheath 60, basket wire 58 and/or the basket 61 while the user grips the handle 30. The knob assembly 44 is rotatable between a non-rotated position and a rotated position (See FIGS. 3A and 3B). The direction that the outer knob 54 is rotated in (i.e., the direction of the arrows 74, 76) generally corresponds to the direction that the basket sheath 60, the basket wire 58 and/or the basket 61 moves relative to the working channel 42 and/or the distal end 29 (not illustrated here) of the medical device 22 (i.e., the direction that the basket wire 58, the basket 61, or both move, deploy, retract, or a combination thereof relative to the basket sheath 60, the working channel 42, the distal end 29 of the medical device 22, or a combination thereof.) The biasing member 68 assists a user in moving the knob assembly 44 from the rotated position to the non-rotated position. While the user grips the handle 30 with the same hand, the user can use a second finger of the same hand to move the mechanism 34 to move, deflect, bend and/or control the tubular portion 40 of the medical device 22.

Figure 6A:
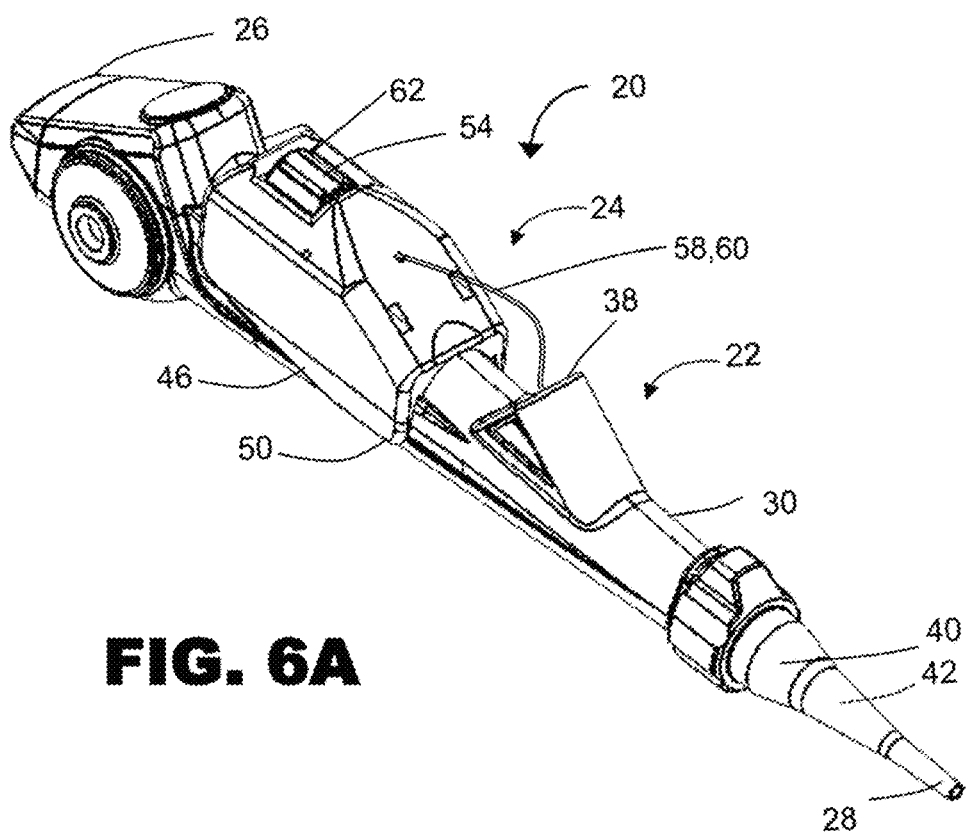
FIG. 6A illustrates a perspective view of a medical system including a medical device and an auxiliary medical device.
Figure 6B:
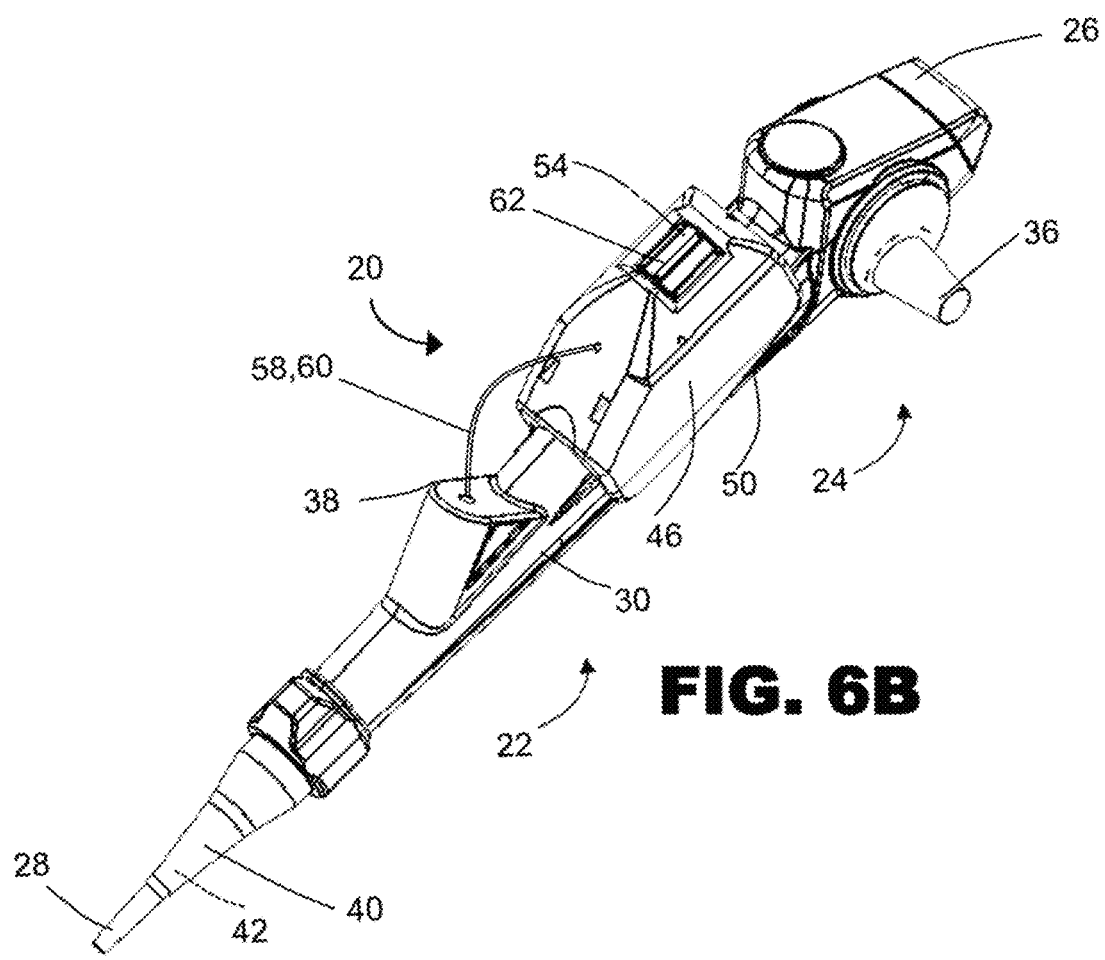
FIG. 6B illustrates a perspective view of a medical system: including a medical device and an auxiliary medical device in accordance with the teachings herein.
Figure 7:
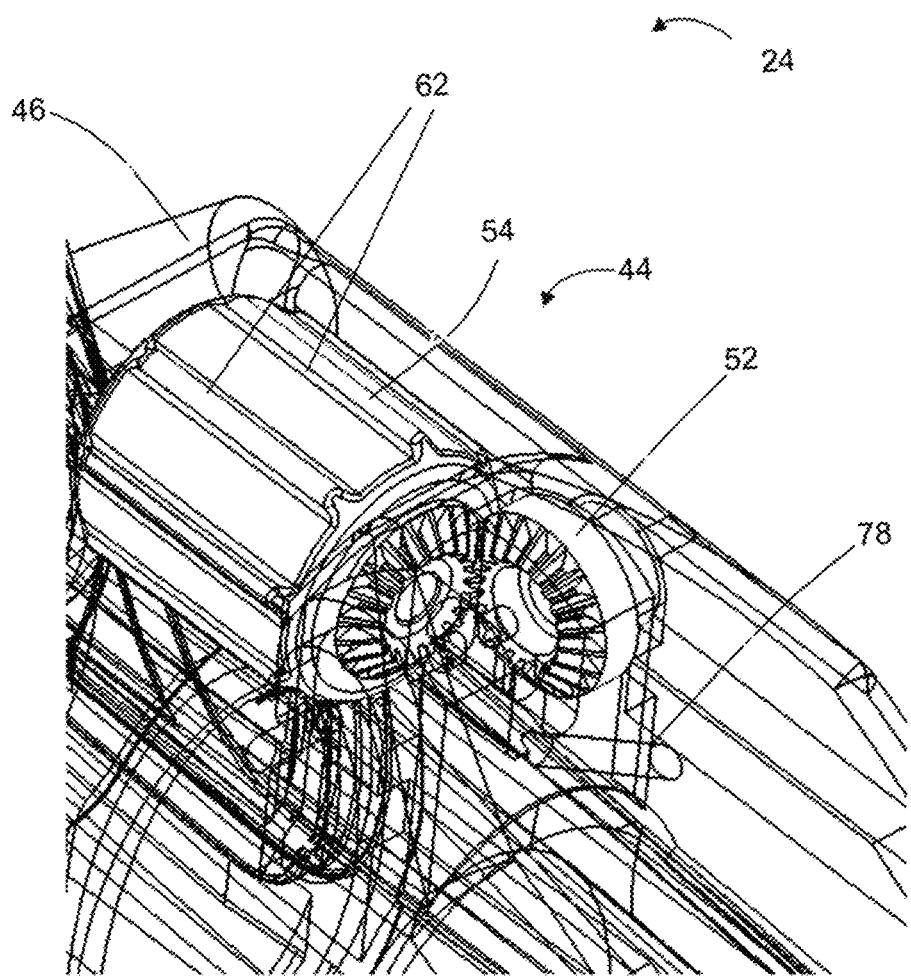
FIG. 7 illustrates a partial detailed view of the auxiliary medical device of FIG. 6B.

FIGS. 6A, 6B, and 7 illustrate a medical system 20 including a medical device 22 and an auxiliary medical device 24. The medical device 22 extends between a proximal end 26 and a distal end 29 (not illustrated here). The proximal end 26 of the medical device 22 includes a handle 30. The handle 30 includes a mechanism 34 (not illustrated here) for moving, deflecting, bending, controlling, or a combination thereof a tubular portion extending from the handle 30. The handle 30 includes a connector port 36 for connecting illumination, video imaging capabilities, or both to the medical system 20, the medical device 22, or both. The handle 30 includes a working channel port 38 providing access to a working channel 42 located within a tubular portion 40 of the medical device 22.

The auxiliary medical device 24 is removably connected to the medical device 22. The auxiliary medical device 24 includes a knob assembly 44 connected to a base 46. The base 46 includes at least one resiliently flexible finger 50 engaging the handle 30 of the medical device 30. The knob assembly 44 includes an inner knob 52 and an outer knob 54 connected to the inner knob 52. The auxiliary medical device 24 is generally aligned with the medical device 22 so that a basket sheath 60, a basket wire 58, and/or a basket 61 (not illustrated here) can be received into the working channel port 38 and into the working channel 42 of the medical device 22. A channel or guide 78 is located near the inner knob 52 to guide the basket sheath 60, the basket wire 58, and/or the basket 61 towards the working channel port 38. The outer knob 54 includes at least one gripping ridge 62 so that a user can grip and rotationally move the outer knob 54 with a first finger and, accordingly, the inner knob 52 and the basket sheath 60 and/or the basket wire 58 disposed there around. The knob assembly 44 is rotatable between a non-rotated position and a rotated position (neither illustrated here) to move the basket sheath 60, the basket 61, and/or the basket wire 58 relative to the distal end 29 of the tubular portion of the medical device 22. The direction that the outer knob 54 is rotated generally corresponds to a direction that is perpendicular to a direction that one or more of the basket sheath 60, the basket wire 58, the basket 61 move relative to the working channel 42 and/or the distal end 29 of the medical device 22 (i.e., the direction that one or more of the basket wire 58, the basket 61 and the basket sheath 60 move, deploy, retract, or a combination thereof relative to the basket sheath 60, the working channel 42, the distal end 29 of the medical device 22, or a combination thereof.) A biasing member 68 (not illustrated here) is in communication with the inner knob 52, the outer knob 54, or both. While the user grips the handle 30 with the same hand, the user can use a second finger of the same hand to move the mechanism 34 to move, deflect, bend and/or control the tubular portion 40 of the medical device 22.

Figure 8A:
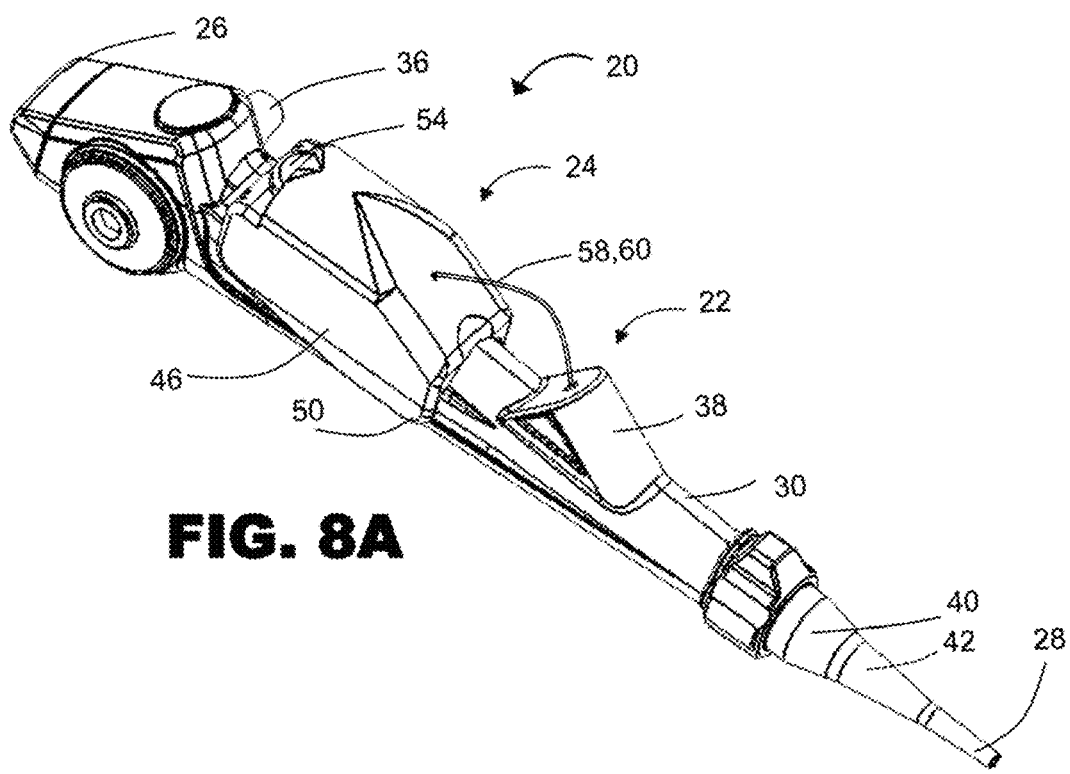
FIG. 8A illustrates a perspective view of a medical system including a medical device and an auxiliary medical device.
Figure 9:
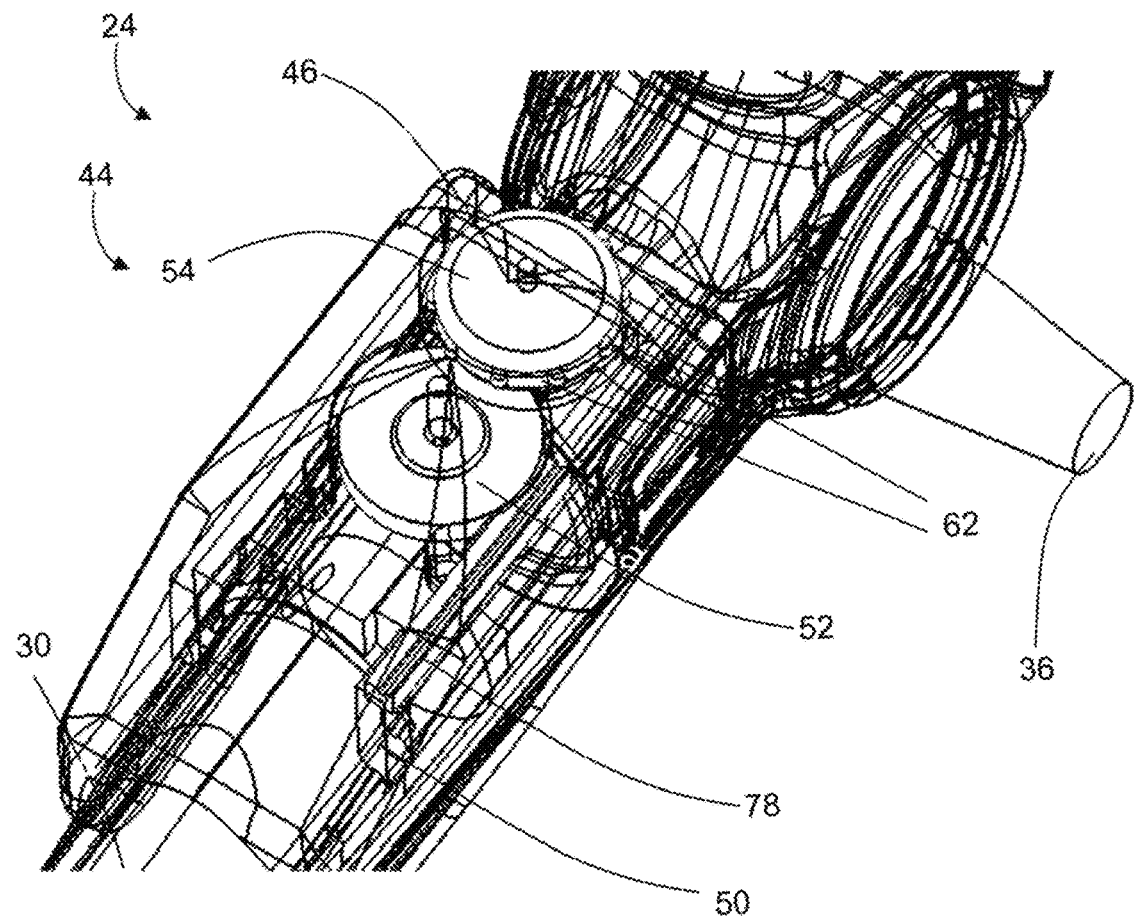
FIG. 9 illustrates a partial detailed view of the auxiliary medical device of FIG. 8B.

FIGS. 8A, 8B, and 9 illustrate a medical system 20 including a medical device 22 and an auxiliary medical device 24. The medical device 22 extends between a proximal end 26 and a distal end 29 (not illustrated here). The proximal end 26 of the medical device 22 includes a handle 30. The handle 30 includes a mechanism 34 (not illustrated here) for moving, deflecting, bending, controlling, or a combination thereof a tubular portion 40 extending from the handle 30. The handle 30 includes a connector port 36 for connecting illumination, video imaging capabilities, or both to the medical system 20, the medical device 22, or both. The handle 30 includes a working channel port 38 providing access to a working channel 42 located within a tubular portion 40 of the medical device 22.

The auxiliary medical device 24 is connected to the medical device 22. The auxiliary medical device 24 includes a knob assembly 44 connected to a base 46. The base 46 includes at least one resiliently flexible finger 50 engaging the handle 30 of the medical device 30. The knob assembly 44 includes an inner knob 52 and an outer knob 54 connected to the inner knob 52. The auxiliary medical device 24 is generally aligned with the medical device 22 so that the basket retrieval device 56, the basket sheath 60, the basket wire 58, and/or the basket 61 can be received into the working channel port 38 and into the working channel 42 of the medical device 22. A channel or guide 78 is located near the inner knob 52 to guide the basket sheath 60, the basket wire 58, and/or the basket 61 towards the working channel port 38. The outer knob 54 includes at least one gripping ridge 62 so that a user can grip and rotationally move the outer knob 54 with a first finger and, accordingly, the basket sheath 60 and basket wire 58 disposed there around. The direction that the outer knob 44 is rotated generally corresponds to a direction that is the same as a direction that the basket sheath 60, basket wire 58, and the basket 61 moves relative to the working channel 42 and/or the distal end 29 of the medical device 22 (i.e., the direction that one or more of the basket wire 58, the basket 61 and the basket sheath 60 move, deploy, retract, or a combination thereof relative to the basket sheath 60, the working channel 42, the distal end 29 of the medical device 22, or a combination thereof.) A biasing member 68 (not illustrated here) is in communication with the knob assembly 44. While the user grips the handle 30 with the same hand, the user can use a second finger of the same hand to move the mechanism 34 to move, deflect, bend and/or control the tubular portion 40 of the medical device 22.

Figure 10:
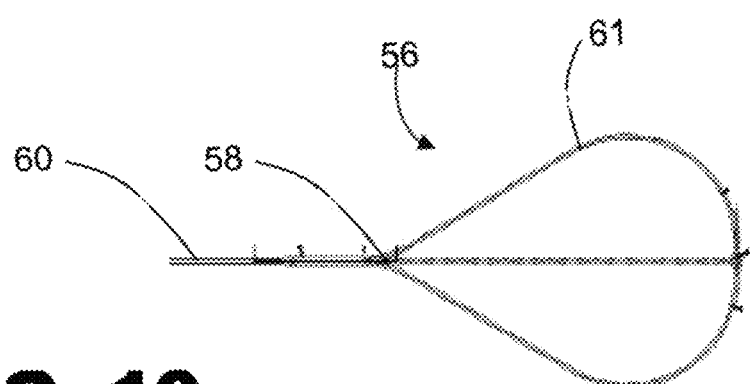
FIG. 10 illustrates a partial side view of a basket retrieval device.
Figure 11:
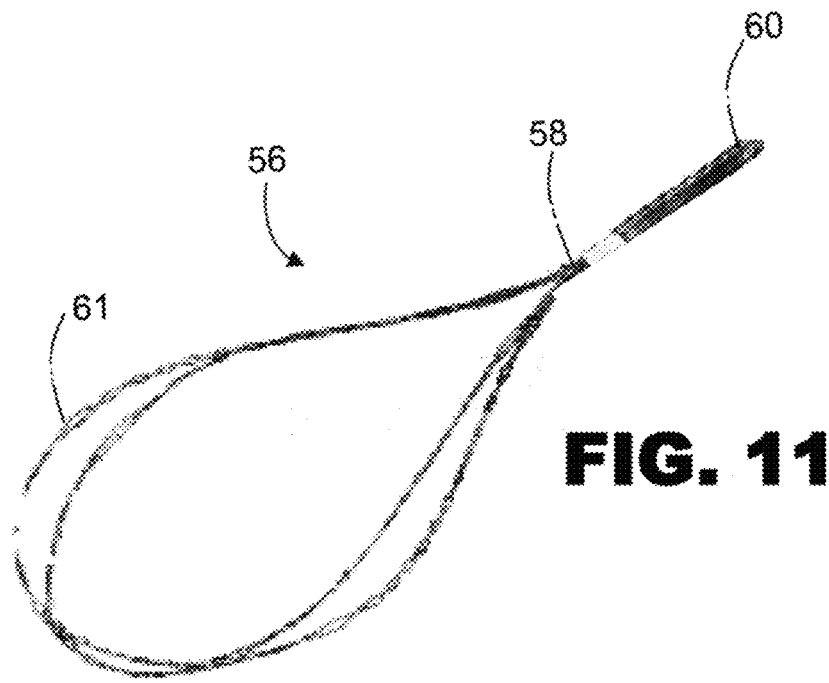
FIG. 11 illustrates a partial perspective view of a basket retrieval device including a basket wire, a basket sheath, and a basket.

FIGS. 10 and 11 illustrate the basket retrieval device 56. The basket retrieval device 56 includes a basket wire 58 disposed within a basket sheath 60. A basket 61 is located at a distal end of the basket wire 58. When the knob assembly 44 (not illustrated here) is rotated to the rotated position, the basket wire 58 and the basket 61 extend and/or expand from within the basket sheath 60 as illustrated and extend out of the tubular portion 40 of the medical device 20 (not illustrated) so that the basket 61 can immobilize and/or retrieve biological matters (e.g., kidney stones, urinary calculi, etc.,). When the knob assembly 44 (not illustrated here) is rotated to the non-rotated position, the basket wire 58 and the basket 61 retract and/or collapse back into the basket sheath 60 and/or the tubular portion 40 of the medical device 20.

Figure 2B:
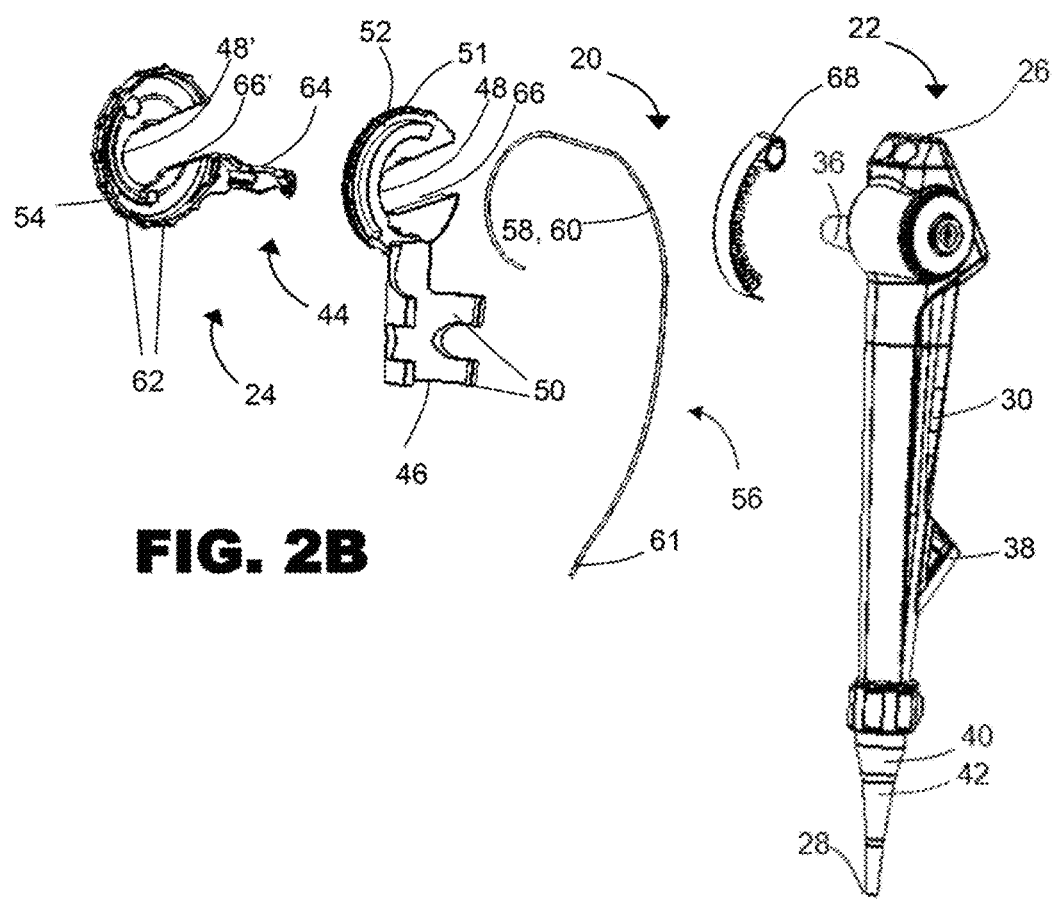
FIG. 2B illustrates an exploded perspective view of a medical system including a medical device and an auxiliary medical device in accordance with the teachings herein.
Figure 14:
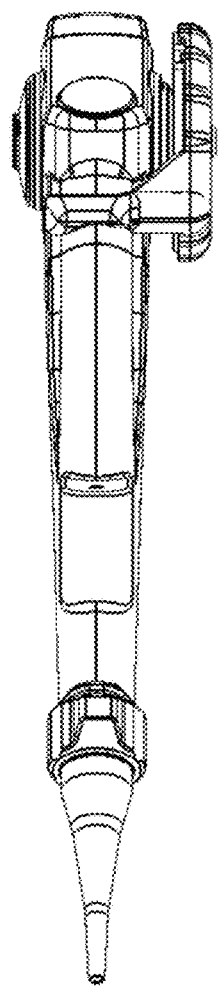
FIG. 14 is a front view of the medical system of FIGS. 4A and 4B.
Figure 15:
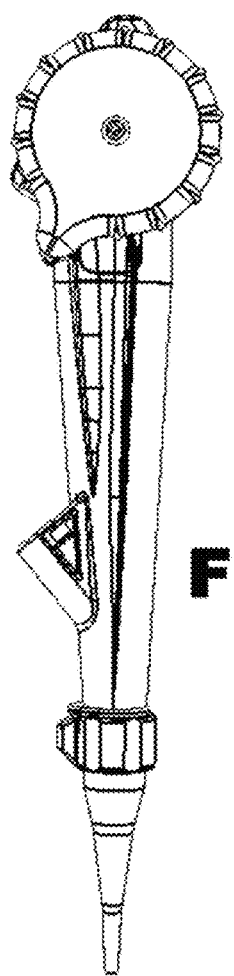
FIG. 15 is a side view of the medical system of FIGS. 4A and 4B.
Figure 16:
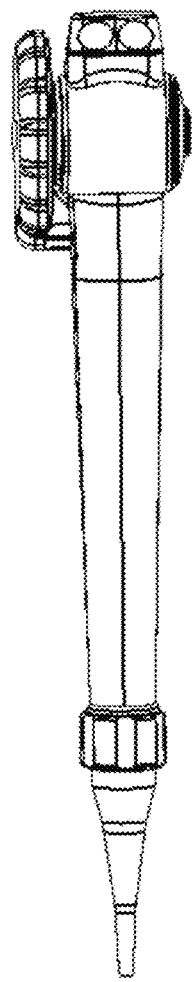
FIG. 16 is a back view of the medical system of FIGS. 4A and 4B.
Figure 17:
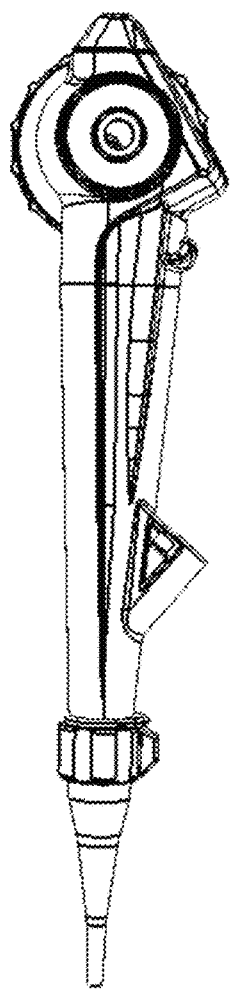
FIG. 17 is a side view of the medical system of FIGS. 4A and 4B.
Figure 18:
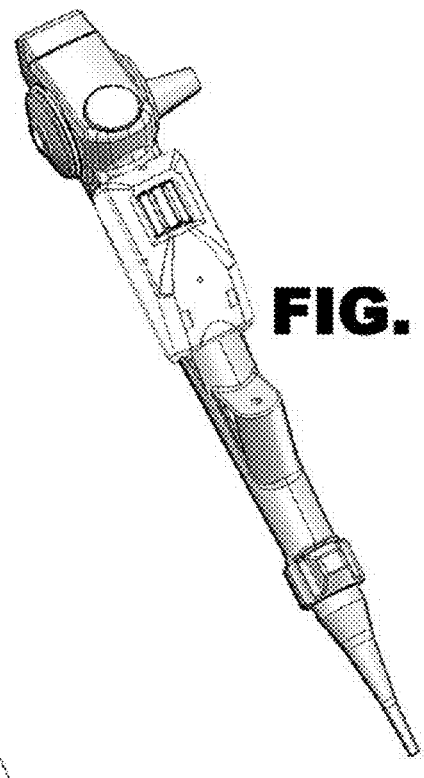
FIG. 18 is a perspective view of the medical system of FIGS. 6A and 6B.
Figure 19:
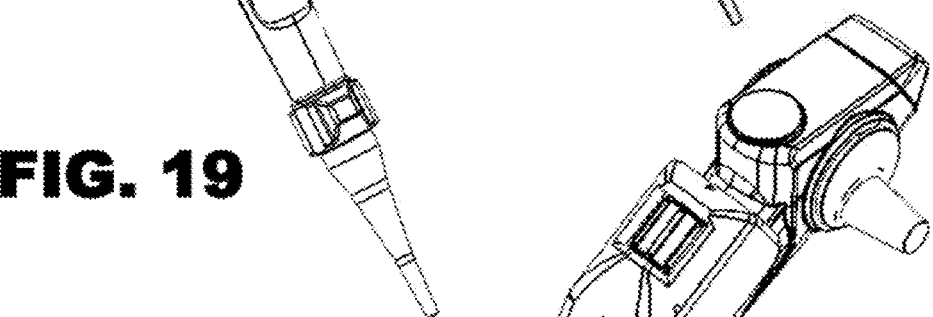
FIG. 19 is a perspective view of the medical system of FIGS. 6A and 6B.
Figure 20:
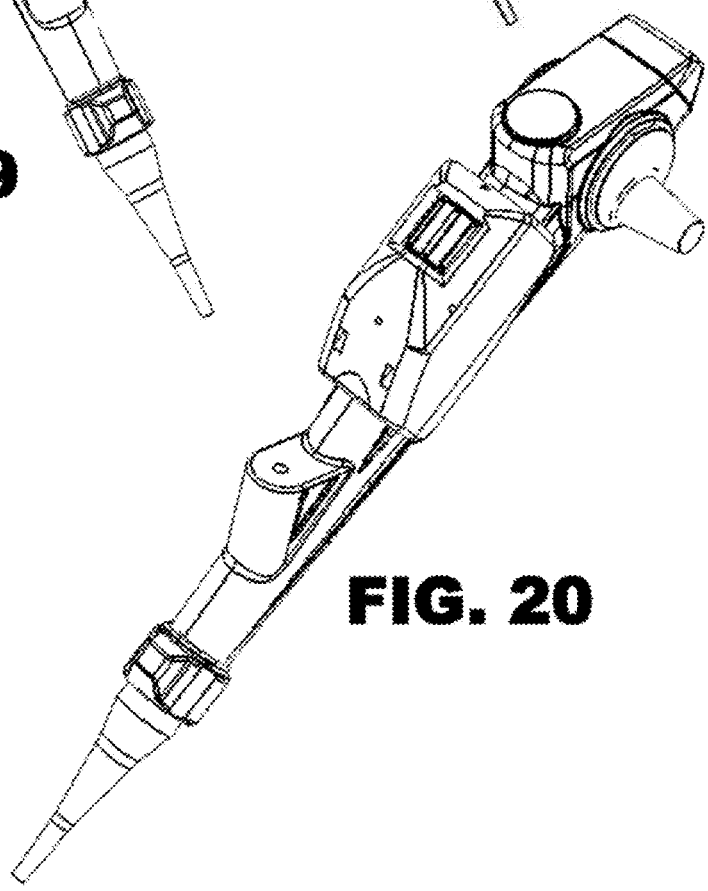
FIG. 20 is a perspective view of the medical system of FIGS. 6A and 6B.
Figure 21:
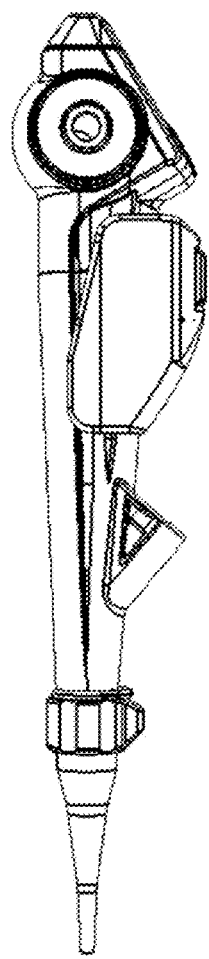
FIG. 21 is a side view of the medical system of FIGS. 6A and 6B.
Figure 22:
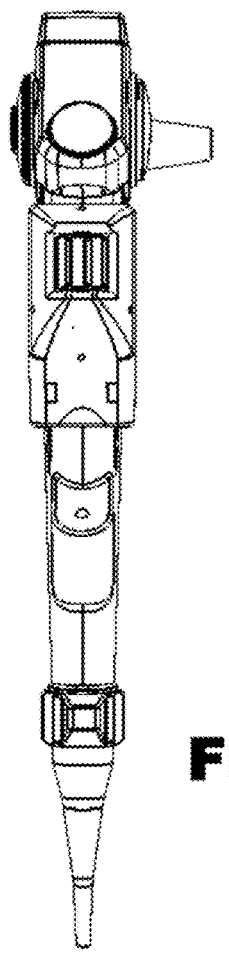
FIG. 22 is a front view of the medical system of FIGS. 6A and 6B.
Figure 23:
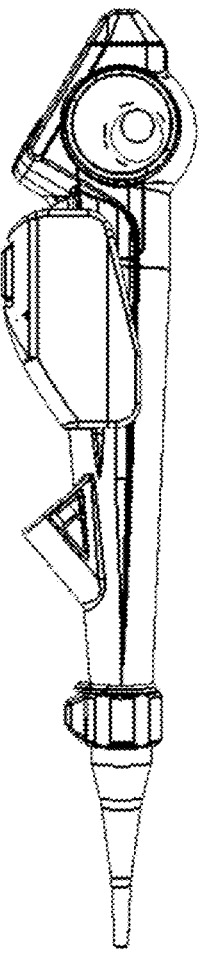
FIG. 23 is a side view of the medical system of FIGS. 6A and 6B.
Figure 24:
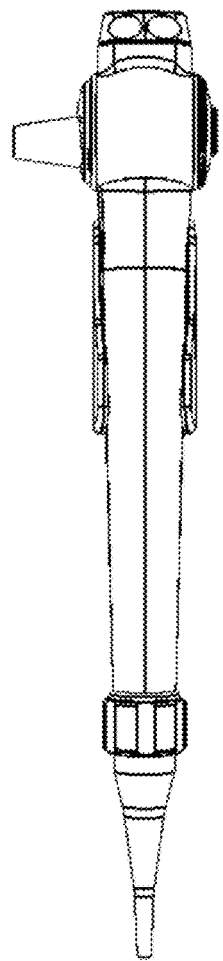
FIG. 24 is a back view of the medical system of FIGS. 6A and 6B.
Figure 25:
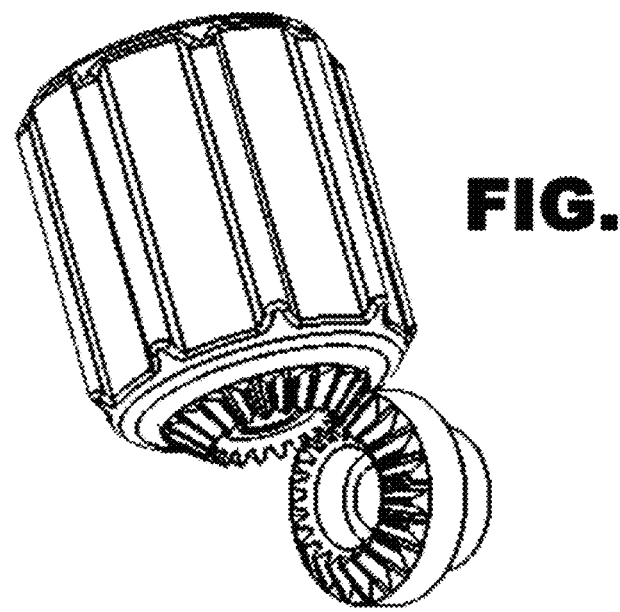
FIG. 25 is a perspective view of the knob assembly of FIGS. 6A, 6B, and 7.
Figure 26:
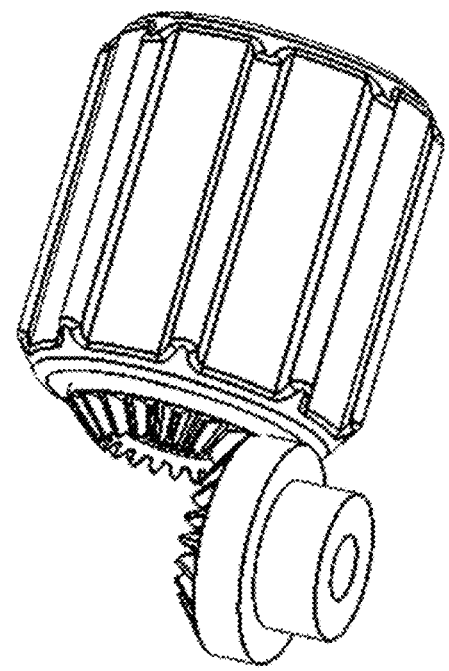
FIG. 26 is a perspective view of the knob assembly of FIGS. 6A, 6B, and 7.
Figures 31, 32:
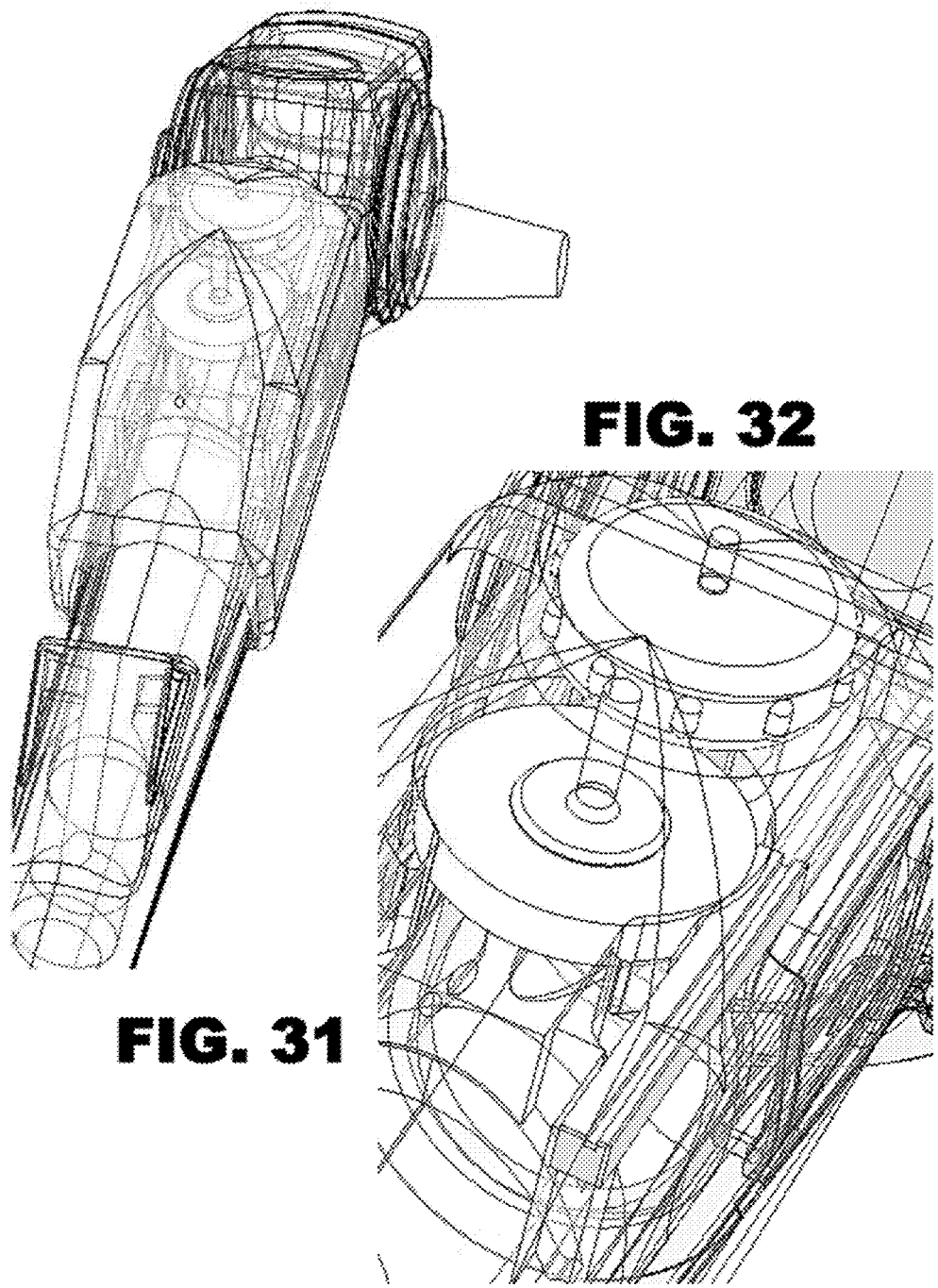
FIG. 31 is a partial perspective and transparent view of the medical system of FIGS. 8A and 8B.
FIG. 32 is a partial perspective and transparent view of the medical system of FIGS. 8A and 8B.
Figure 33:
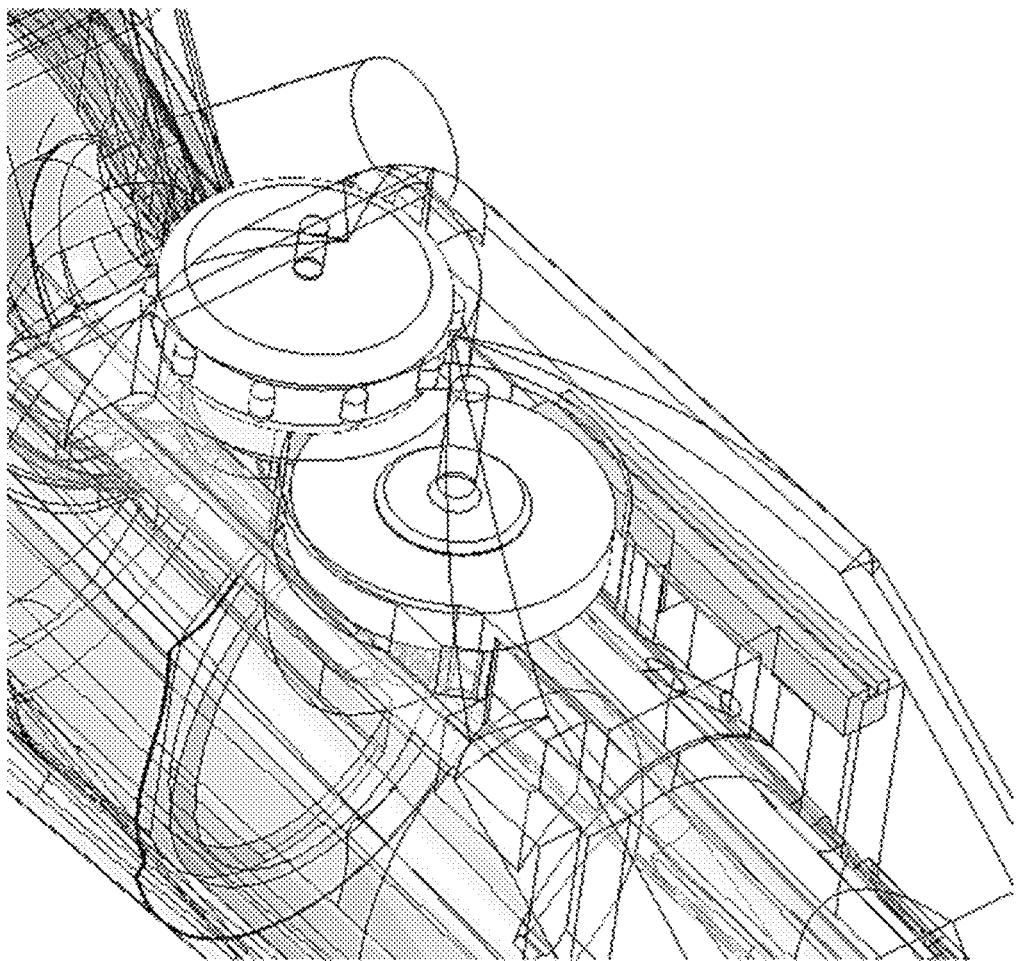
FIG. 33 is a partial perspective and transparent view of the medical system of FIGS. 8A and 8B.
Figures 34, 35:
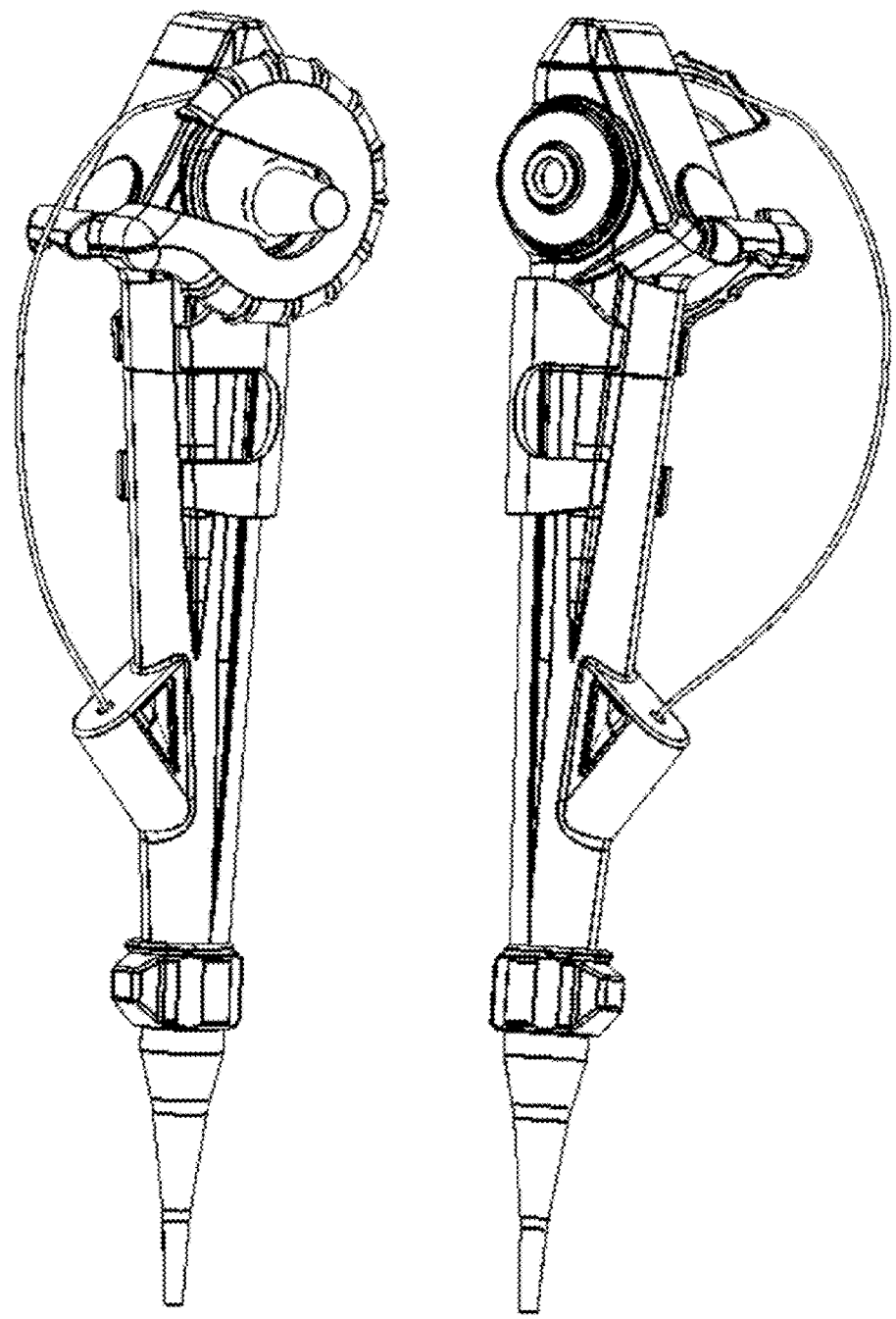
FIG. 34 illustrates an assembled perspective view of the medical system of FIGS. 2A and 2B.
FIG. 35 illustrates an assembled perspective view of the medical system of FIGS. 2A and 2B.
Figure 37A:
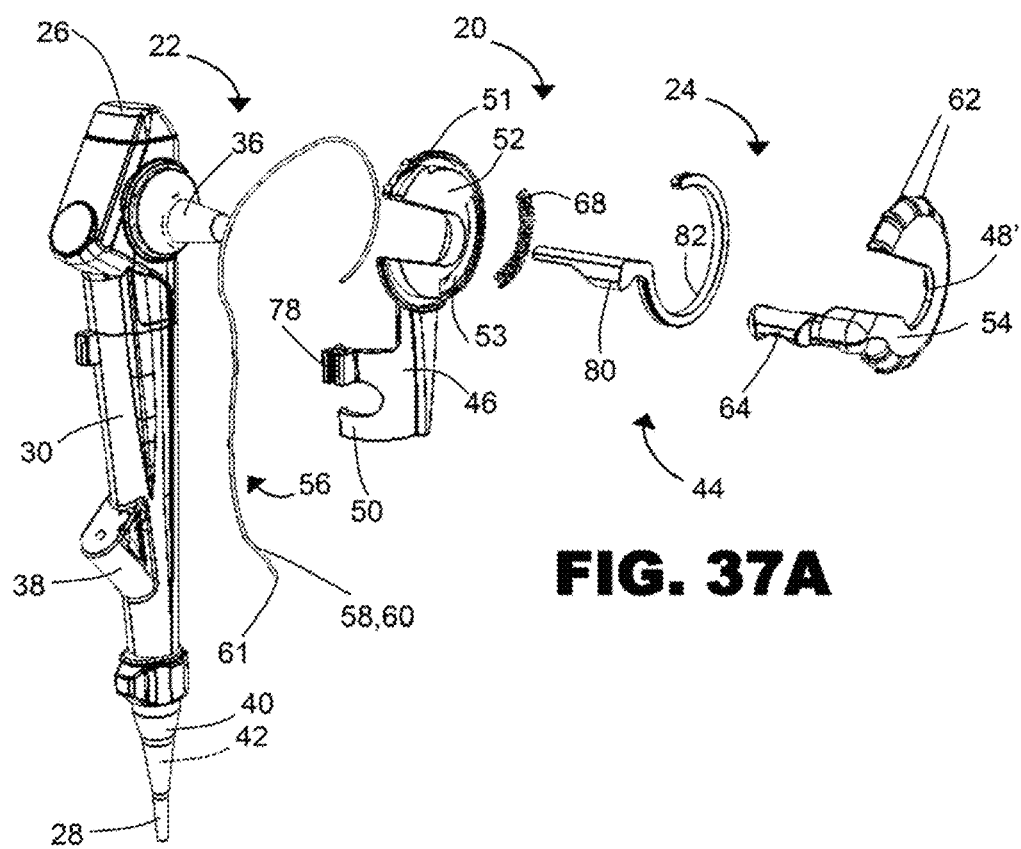
FIG. 37A illustrates an exploded perspective of FIG. 36A.
Figure 37B:
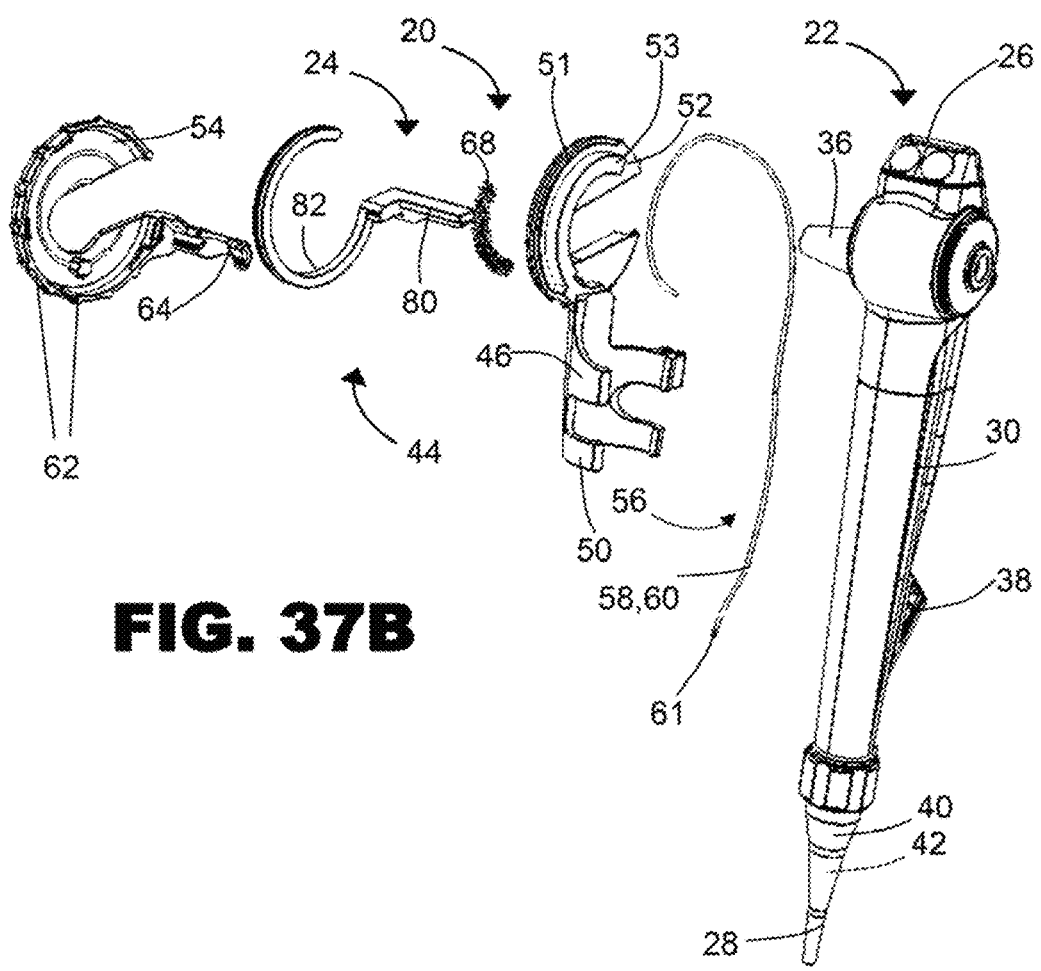
FIG. 37B illustrates an exploded perspective view of FIG. 36B.

FIG. 12A illustrates an assembled side view of the medical system of FIGS. 2A and 2B. FIG. 12B illustrates an assembled front view of the medical system of FIGS. 2A and 2B. FIG. 13A illustrates an assembled side view of the medical system of FIGS. 2A and 2B. FIG. 13B illustrates an assembled back view of the medical system of FIGS. 2A and 2B. FIG. 14 is a front view of the medical system of FIGS. 4A and 4B. FIG. 15 is a side view of the medical system of FIGS. 4A and 4B. FIG. 16 is a back view of the medical system of FIGS. 4A and 4B. FIG. 17 is a side view of the medical system of FIGS. 4A and 4B. FIG. 18 is a perspective view of the medical system of FIGS. 6A and 6B. FIG. 19 is a perspective view of the medical system of FIGS. 6A and 6B. FIG. 20 is a perspective view of the medical system of FIGS. 6A and 6B. FIG. 21 is a side view of the medical system of FIGS. 6A and 6B. FIG. 22 is a front view of the medical system of FIGS. 6A and 6B. FIG. 23 is a side view of the medical system of FIGS. 6A and 6B. FIG. 24 is a back view of the medical system of FIGS. 6A and 6B. FIG. 25 is a perspective view of the knob assembly of FIGS. 6A, 6B, and 7. FIG. 26 is a perspective view of the knob assembly of FIGS. 6A, 6B, and 7. FIG. 27 is a side view of the medical system of FIGS. 8A and 8B. FIG. 28 is a front view of the medical system of FIGS. 8A and 8B. FIG. 29 is a side view of the medical system of FIGS. 8A and 8B. FIG. 30 is a back view of the medical system of FIGS. 8A and 8B. FIG. 31 is a partial perspective and transparent view of the medical system of FIGS. 8A and 8B. FIG. 32 is a partial perspective and transparent view of the medical system of FIGS. 8A and 8B. FIG. 33 is a partial perspective and transparent view of the medical system of FIGS. 8A and 8B. FIG. 34 illustrates an assembled perspective view of the medical system of FIGS. 2A and 2B. FIG. 35 illustrates an assembled perspective view of the medical system of FIGS. 2A and 2B.

FIGS. 36A, 36B, 37A, and 37B illustrate a medical system 20 including a medical device 22 and an auxiliary medical device 24. The medical device 22 extends between a proximal end 26 and a distal end 29 (not illustrated here). The proximal end 26 of the medical device 22 includes a handle 30. The handle 30 includes a mechanism 34 (not illustrated here) for moving, deflecting, bending, controlling, or a combination thereof a tubular portion 40 extending from the handle 30. The handle 30 includes a connector port 36 for connecting illumination, video imaging capabilities, or both to the medical system 20, the medical device 22, or both. The handle 30 includes a working channel port 38 providing access to a working channel 42 located within a tubular portion 40 of the medical device 22.

The auxiliary medical device 24 is removably connected to the medical device 22. The auxiliary medical device 24 includes a knob assembly 44 connected to a base 46. The base 46 includes at least one resiliently flexible finger 50 engaging the handle 30 of the medical device 30. The knob assembly 44 includes an inner knob 52, an outer knob 54 connected to the inner knob 52, and an auxiliary lever 80 including a circular portion 82 located between the inner knob 52 and the outer knob 54. The auxiliary medical device 24 is generally aligned with the medical device 22 so that a basket sheath 60, a basket wire 58, and/or a basket 61 can be received into the working channel port 38 and into the working channel 42 of the medical device 22. A wire guide 78 on the base 46 can direct or guide the basket wire 58, the basket sheath 60, or both into the working channel port 38. The outer knob 54 includes at least one gripping ridge 62 so that a user can grip and rotationally move the outer knob 54 with a first finger and, accordingly, the inner knob 52 and the basket sheath 60 and/or the basket wire 58 disposed there around. A user can manipulate the auxiliary lever 80 with a first finger or a second finger to move the inner knob 52 and the outer knob 54 individually or together. The knob assembly 44 is rotatable between a non-rotated position and a rotated position (neither illustrated here) to move the basket sheath 60, the basket 61, and/or the basket wire 58 relative to the distal portion 28 of the tubular portion 40 of the medical device 22. The direction that the outer knob 54 is rotated generally corresponds to a direction that one or more of the basket sheath 60, the basket wire 58, the basket 61 move relative to the working channel 42 and/or the distal portion 28 of the medical device 22 (i.e., the direction that one or more of the basket wire 58, the basket 61 and the basket sheath 60 move, deploy, retract, or a combination thereof relative to the basket sheath 60, the working channel 42, the distal portion 28 of the medical device 22, or a combination thereof.) A biasing member 68 is in communication with the inner knob 52, the outer knob 54, or both. While the user grips the handle 30 with the same hand, the user can use a second finger of the same hand to move the mechanism 34 to move, deflect, bend and/or control the tubular portion 40 of the medical device 22.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values that are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A medical system comprising:
   I. a medical device, the medical device including a handle and a mechanism for moving a distal end of the medical device, the medical device including a connector port projecting from the handle, the connector port is adapted to connect to a light source and to provide illumination to the medical system; and
   II. an auxiliary medical device, the auxiliary medical device comprising:
      i. a basket retrieval device including a basket sheath disposed over a basket wire, the basket sheath, the basket wire, or both are received into a working channel of the medical device;
      ii. a knob assembly in communication with the basket retrieval device, the knob assembly includes an opening, the connector port of the medical device projects through the opening and the knob assembly, the knob assembly comprises a circular member that is rotatable about an outer surface of the connector port so that the basket sheath, the basket wire, or both move within the working channel of the medical device; and
      iii. a base connected to the knob assembly, the base removably connecting the auxiliary medical device to the handle of the medical device,
   wherein the medical device is an endoscope, a ureteroscope, or both, and the basket retrieval device includes a basket connected to a distal end of the basket wire,
   wherein the handle and the base are configured to be simultaneously gripped with a hand of a user,
   wherein the mechanism is configured to be moved with a first finger of the hand to move the distal end of the medical device and the knob assembly is configured to be rotated with a second finger of the hand to move the basket sheath, the basket wire, or both relative to the distal end of the medical device,
   wherein moving the mechanism with the first finger causes the distal end of the medical device to deflect, bend, or both,
   wherein rotating the knob assembly with the second finger in a first direction causes the basket wire and the basket to deploy from the basket sheath, the distal end of the medical device or both so that an object can be captured,
   wherein rotating the knob assembly with the second finger in a second direction causes the basket wire and the basket to collapse, retract, or both into the basket sheath, the distal end of the medical device, or both, and
   wherein a biasing member that is in communication with the knob assembly helps rotate the knob assembly from the first direction back to the second direction.

2. The medical system of claim 1, wherein the base includes at least one resiliently deflectable finger at least partially surrounding an outer circumference of the handle removably connecting the auxiliary medical device to the handle.

3. The medical system of claim 1, wherein the knob assembly includes an inner knob in communication with the basket retrieval device and an outer knob engaging the inner knob, the outer knob includes a gripping ridge, a lever, or both,
 wherein the outer knob is rotatable in the first direction, the second direction, or both by engaging the gripping ridge, the lever, or both with the second finger,
 wherein the outer knob includes a circular portion, and the inner knob comprises a circular portion, and
 wherein the circular portion of the outer knob is arranged on top of the circular portion of the inner knob.

4. The medical system of claim 1, wherein the knob assembly includes an auxiliary lever, and inner knob, and an outer knob, the auxiliary lever comprises a circular portion, the inner knob comprises a circular portion, and the outer knob comprises a circular portion, the circular portion of the auxiliary lever is sandwiched between the circular portion of the inner knob and the circular portion of the outer knob,
 wherein the auxiliary lever is rotatable with the first finger or the second finger so that one or both of the inner knob and the outer knob rotate, and
 wherein movement of the auxiliary lever causes:
  i. the basket wire and the basket to collapse, retract, or both into the basket sheath, the distal end of the medical device, or both, and/or
  ii. the distal end of the medical device to move.

5. The medical system of claim 1, wherein the opening of the knob assembly is a C-shaped slot having an open portion defined in a portion of an outer circumference of the knob assembly.

6. The medical system of claim 3, wherein first direction is generally the same as a direction that the basket wire and the basket deploy from the basket sheath, the distal end of the medical device, or both.

7. The medical system of claim 1, wherein the biasing member is a circular spring.

8. The medical system of claim 7, wherein the knob assembly comprises an inner knob, the inner knob includes a groove for engaging the biasing member.

9. The medical system of claim 1, wherein the medical device includes a viewing device that is adapted for the user to view an area of interest located at the distal end of the medical device.

10. The medical system of claim 1, wherein the knob assembly and the mechanism are located on opposing sides of the medical device.

11. The medical system of claim 1, wherein the connector port is a plug that is adapted to connect video imaging to the medical system.

12. The medical system of claim 1, wherein the base includes a wire guide for guiding the basket wire into a working channel port on the medical device.

13. A medical system comprising:
 a medical device including a handle and a mechanism for moving a distal end of the medical device; and
 an auxiliary medical device comprising:
  a basket retrieval device including a basket sheath disposed over a basket wire,
  a knob assembly, the knob assembly comprises an inner knob that has a groove at least partially extending around a circumference thereof, the groove engages at least a portion of the basket retrieval device, the knob assembly includes an opening that surrounds a connector port that projects from the handle of the medical device, the connector port is a plug that is adapted to connect and provide illumination and/or video imaging to the medical device, the knob assembly is rotatable about an outer surface of the connector port so that the basket sheath, the basket wire, or both move within the working channel of the medical device; and
  a base connected to the knob assembly, the base removably connecting the auxiliary medical device to the handle of the medical device,
 wherein the medical device is an endoscope, a ureteroscope, or both, and the basket retrieval device includes a basket connected to a distal end of the basket wire,
 wherein the base of the auxiliary medical device is attached to the handle of the medical device so that both the base and the handle are configured to be simultaneously gripped with a hand of a user,
 wherein the mechanism is configured to be moved so that the distal end of the medical device, and the knob assembly is configured to be rotated to move the basket sheath, the basket wire, or both relative to the distal end of the medical device,
 wherein rotating the knob assembly in a first direction causes the basket wire and the basket to deploy from the basket sheath, the distal end of the medical device or both, and rotating the knob assembly in a second direction causes the basket wire and the basket to collapse, retract, or both into the basket sheath, the distal end of the medical device, or both,
 wherein a circular spring is in communication with the knob assembly helps rotate the knob assembly from the second direction back to the first direction, and
 wherein the knob assembly and the mechanism are located on opposing sides of the handle of the medical device.

14. The medical system of claim 13, wherein the knob assembly includes an auxiliary lever and an outer knob, the auxiliary lever is located between the inner knob and the outer knob,
 wherein rotation of the auxiliary lever causes:
  i. the basket wire and the basket to collapse, retract, or both into the basket sheath, the distal end of the medical device, or both, and/or
  ii. the distal end of the medical device to move.

15. The medical system according to claim 1, wherein the knob assembly comprises an inner knob and an outer knob,
 wherein outer knob includes a circular portion, and the outer knob comprises a circular portion, and
 wherein the circular portion of the outer knob is arranged on top of the circular portion of the outer knob.

16. The medical system according to claim 15, wherein the opening of the knob assembly comprises a C-shaped slot defined in the circular portion of the outer knob, and a C-shaped slot defined in the inner circular portion of the inner knob.

17. The medical system according to claim 16, wherein the C-shaped slot defined in the circular portion of the outer knob comprises an open portion defined in a portion of an outer circumference of the outer knob, and the C-shaped slot defined in the circular portion of the inner knob comprises an open portion defined in a portion of an outer circumference of the inner knob, and
 wherein the C-shaped slot defined in the circular portion of the outer knob is arranged on top of the C-shaped slot defined in the circular portion of the inner knob.

18. The medical system of claim 1, wherein the knob assembly includes an auxiliary lever, an inner knob, and an outer knob,
- wherein the auxiliary lever comprises a circular portion, the inner knob comprises a circular portion, and the outer knob comprises a circular portion, and
- wherein the circular portion of the auxiliary lever is sandwiched between the circular portion of the inner knob and the circular portion of the outer knob.

19. The medical system according to claim 13, wherein the outer knob includes a circular portion, and the inner knob comprises a circular portion,
- wherein the circular portion of the outer knob is arranged on top of the circular portion of the inner knob.

20. The medical system according to claim 19, wherein the opening of the knob assembly comprises a slot defined in the circular portion of the outer knob and a slot defined in the circular portion of the inner knob.

\* \* \* \* \*